(12) United States Patent
Vats et al.

(10) Patent No.: US 11,353,450 B2
(45) Date of Patent: Jun. 7, 2022

(54) ANALYTE DETECTION USING RAMAN SPECTROSCOPY

(71) Applicant: MedMira Inc., Halifax (CA)

(72) Inventors: Neeraj Vats, Upper Tantallon (CA); Hok Ping Hui, Halifax (CA)

(73) Assignee: MedMira Inc., Halifax (CA)

( * ) Notice: Subject to any disclaimer, the term of this patent is extended or adjusted under 35 U.S.C. 154(b) by 569 days.

(21) Appl. No.: 16/464,127

(22) PCT Filed: Nov. 25, 2017

(86) PCT No.: PCT/CA2017/051412
§ 371 (c)(1),
(2) Date: May 24, 2019

(87) PCT Pub. No.: WO2018/094528
PCT Pub. Date: May 31, 2018

(65) Prior Publication Data
US 2019/0376962 A1 Dec. 12, 2019

(30) Foreign Application Priority Data
Nov. 25, 2016 (CA) .................................. CA 2949634

(51) Int. Cl.
*G01N 33/543* (2006.01)
*G01N 21/65* (2006.01)
*G01N 33/532* (2006.01)

(52) U.S. Cl.
CPC ..... *G01N 33/54346* (2013.01); *G01N 21/658* (2013.01); *G01N 33/532* (2013.01)

(58) Field of Classification Search
CPC ........... G01N 33/54346; G01N 21/658; G01N 33/532; G01N 21/65; G01N 21/77; B82Y 30/00
See application file for complete search history.

(56) References Cited

U.S. PATENT DOCUMENTS

| 8,025,850 B2 | 9/2011 | Chan | |
|---|---|---|---|
| 2005/0089901 A1* | 4/2005 | Porter | G01N 21/658 530/391.1 |
| 2011/0256638 A1 | 10/2011 | Chan et al. | |

FOREIGN PATENT DOCUMENTS

CA 2566123 A1 12/2005

OTHER PUBLICATIONS

Albrecht et al., "Anomalously Intense Raman Spectra of Pyridine at a Silver Electrode," Journal of the American Chemical Society, Jul. 1977, vol. 99 (15), pp. 5215-5217.
(Continued)

*Primary Examiner* — Jennifer Wecker
*Assistant Examiner* — Oyeleye Alexander Alabi
(74) *Attorney, Agent, or Firm* — Borden Ladner Gervais LLP; Kathleen E. Marsman

(57) ABSTRACT

Methods and Raman detection agents for detecting an analyte in a sample are provided. Methods described herein may comprise steps of providing a 3D diagnostic substrate presenting a capture agent for the analyte or an analyte complex; exposing the sample to the substrate and to a Raman detection agent, allowing analyte in the sample to bind to the capture agent of the diagnostic substrate and an affinity component of the Raman detection agent; and detecting the Raman detection agent bound to the 3D diagnostic substrate by Raman spectroscopy, thereby detecting the presence of the analyte in the sample. Raman detection agents described herein may comprise a Raman signal-enhancing metal nanoparticle carrying both a Raman reporter and an affinity component for binding to the analyte or the complex formed between the analyte and the capture agent on the 3D diagnostic substrate.

18 Claims, 22 Drawing Sheets

(56) References Cited

OTHER PUBLICATIONS

Choi et al., "Quantitative Analysis of Thyroid-stimulating Hormone (TSH) Using SERS-Based Lateral Flow Immunoassay," Sensors and Actuators B: Chemical, Mar. 2017, vol. 240, pp. 358-364. (DOI: 10.1016/j.snb.2016.08.178).

Crawford et al., "Sampling Error: Impact on the Quantitative Analysis of Nanoparticle-Based Surface-Enhanced Raman Scattering Immunoassays," Analytical Chemistry, May 2016, vol. 88 (12), pp. 6515-6522. (DOI: 10.1021/acs.analchem.6b01263).

International Patent Application No. PCT/CA2017/051412, International Preliminary Report on Patentability dated Jun. 6, 2019.

International Patent Application No. PCT/CA2017/051412, International Search Report and Written Opinion dated Jan. 22, 2018.

Jeanmaire et al., "Surface Raman Spectroelectrochemistry: Part I. Heterocyclic, Aromatic, and Aliphatic Amines Adsorbed on the Anodized Silver Electrode," Journal of Electroanalytical Chemistry and Interfacial Electrochemistry, Nov. 1977, vol. 84 (1), pp. 1-20.

Li et al., "Ultrahigh Affinity Raman Probe for Targeted Live Cell Imaging of Prostate Cancer", Chemical Science, Jul. 2016, vol. 7(11), pp. 6779-6785, DOI: 10.1039/c6sc01739h, URL: http://pubs.rsc.org/en/content/articlehtml/2016/sc/c6sc01739h.

Meneghetti et al., "Plasmonic Nanostructures for SERRS Multiplexed Identification of Tumor-Associated Antigens", Small, Dec. 2012, vol. 8(24), pp. 3733-3738, DOI: 10.1002/smll.201201196, URL: http://onlinelibrary.wiley.com/doi/10.1002/smll.201290138/full.

Smolsky et al., "Surface-Enhanced Raman Scattering-Based Immunoassay Technologies for Detection of Disease Biomarkers", Biosensors, Jan. 2017, vol. 7(1), pp. 1-21, doi:10.3390/bios7010007, URL: http://www.mdpi.com/2079-6374/7/1/7.

Zheng et al., "Surface-Enhanced Raman Scattering of 4-Aminothiophenol in Assemblies of Nanosized Particles and the Macroscopic Surface of Silver", Langmuir, Jul. 2003, vol. 19(3), pp. 632-636, doi: 10.1021/la011706p, URL http://pubs.acs.org/doi/pdf/10.1021/la011706p.

* cited by examiner

Top View

FIGURE 12

| Sample | Water (µL) | Sample conc. (µM) | Sample (µL) | Gold nanorods (AuR) before PA conjugation | Raman Reporter (DAPT) added after PA conjugation | Ea-1 to Ea-7 | SERS Observed | |
|---|---|---|---|---|---|---|---|---|
| 1 | 990 | 10 | 1 | 195µL, 0.1mM | | No, too agg. | No | Approach A |
| 2 | 990 | 10 | 1 | 50µL, 0.1mM | | Yes | No | |
| 3 | 990 | 10 | 1 | 10µL, 0.1mM | | Yes | No | |
| 4 | 990 | 10 | 1 | | 195µL, 0.1mM | Yes | Yes | |
| 5 | 990 | 10 | 1 | | 50µL, 0.1mM | Yes | No | Approach B |
| 6 | 990 | 10 | 1 | | 10µL, 0.1mM | Yes | No | |
| 7 | 990 | 10 | 1 | 0 | 0 | Yes | No | Control |

ANALYTE DETECTION USING RAMAN SPECTROSCOPY

CROSS REFERENCE TO RELATED APPLICATIONS

This application claims the benefit of priority of Canadian Patent Application No. 2,949,634 filed Nov. 25, 2016, which is hereby incorporated by reference.

FIELD OF INVENTION

The present invention generally relates to methods and agents for the detection of analytes. More specifically, the present invention relates to methods and agents for determining the presence of an analyte in a sample using surface enhanced Raman spectroscopy.

BACKGROUND

Diagnostic assays continue to play an increasingly important role in modern medicine and many other analytically oriented fields. Rapid advances in diagnostic and analytical technologies have enabled quick turn-around times for obtaining results, and vastly increased our ability to diagnose diseases, even at early stages where detection has previously proven difficult. Diagnostic assays requiring minimal equipment and technical expertise to perform are becoming increasingly sought after, particularly with the ongoing drive toward personalized medicine. These assays have the potential to enable widespread disease screening in a cost-effective manner, and to improve early detection rates of a variety of diseases.

Successful diagnostic assays and methods aim to provide results which are both reliable and reproducible. Given that different diagnostic applications typically involve working with different sample types, different analytes, and different diagnostic read-out parameters, the development of a reliable and reproducible diagnostic assay platform which is broadly applicable across a variety of different disease applications has thus far proven quite difficult. Such endeavours can become even more complicated when quantitative results, as opposed to qualitative results, are required for diagnosis.

Most diagnostic assays rely on the detection of, or absence of detection of, a particular disease-linked analyte (also commonly referred to as a disease marker) in a sample obtained from the subject to be tested. Such analytes may include, for example, virus or bacterial proteins or nucleic acids, host or pathogen-derived biomolecules or metabolites, or other disease-linked proteins or biomarkers. Antibodies are a particularly common analyte used in diagnostic assays, as the presence of pathogen-specific antibodies in a subject typically signals that the subject has been exposed to, or is infected with, that particular pathogen.

In many cases, qualitative diagnostic assays are sufficient for screening purposes. However, quantitative diagnostic assays are frequently desired, particularly where determining analyte levels in a subject can inform diagnosis. A number of analytical tools have been developed which allow for qualitative and quantitative read-outs. Examples include high performance liquid chromatography (HPLC), mass spectroscopy, IR, UV-VIS, NMR, and ELISA, among others.

Raman spectroscopy represents an example of an analytical tool which may be used for both qualitative and quantitative analysis. Handheld, battery operated Raman spectrometers are already on the market at cost-effective price points, demonstrating that these analytical tools may be useful even as part of diagnostic assays being employed in remote locations without reliable access to electricity. Raman spectroscopy is also appealing due to the sensitivity and versatility of this analytical tool. Further, Surface-Enhanced Raman spectroscopy (SERS) techniques are in development to provide excellent sensitivity through enhanced signal intensity and/or detection.

Unfortunately, existing diagnostic assay platforms attempting to utilize Raman spectroscopy analytical tools have been hampered by poor reliability and/or reproducibility. Results can vary even when taking readings from different regions of the same diagnostic assay reaction zone in certain examples.

Alternative, additional, and/or improved diagnostic assays, methods, devices, and reagents are desirable.

SUMMARY OF INVENTION

Described herein are methods for determining the presence of an analyte in a sample using SERS spectroscopy. It has now been found that by 1) exposing the sample to a diagnostic substrate presenting a capture agent for the analyte, and then exposing the diagnostic substrate to a Raman detection agent comprising a Raman signal-enhancing metal nanoparticle carrying both a Raman reporter and an affinity component for binding the analyte (or a complex formed between the analyte and the capture agent); or by 2) exposing the sample to a Raman detection agent presenting an affinity component for the analyte, and then exposing the resulting complex to a diagnostic substrate presenting a capture agent for the analyte or the analyte-Raman detection agent complex; or by 3) simultaneously exposing the sample to the diagnostic substrate and the Raman detection agent, wherein the capture agent of the diagnostic substrate is specific for the analyte or the analyte-Raman detection agent complex and the affinity component of the Raman detection agent is specific for the analyte or the complex formed between the analyte and the capture agent; wherein the diagnostic substrate of 1), 2), or 3) may be a 3D diagnostic substrate, reliable and reproducible analyte detection may be achieved using Raman spectroscopy analysis. Also described herein are Raman detection agents and diagnostic substrates useful in such diagnostic assays and methods, which may allow for analyte detection with sensitivity and/or reproducibility through SERS.

In an embodiment, there is provided herein a method for detecting the presence of an analyte in a sample from a subject or source, said method comprising:

providing a diagnostic substrate presenting a capture agent;

exposing the sample to the diagnostic substrate, allowing analyte in the sample, if present, to bind the diagnostic substrate via the capture agent presented thereon which is specific for the analyte;

exposing the diagnostic substrate to a Raman detection agent which binds to the diagnostic substrate via binding to the analyte, or to a complex formed between the analyte and the capture agent, if the analyte is present; and detecting whether the Raman detection agent bound to the diagnostic substrate using Raman spectroscopy, whereby detection of Raman detection agent bound to the diagnostic substrate indicates the presence of the analyte in the sample;

wherein the Raman detection agent comprises a Raman signal-enhancing metal nanoparticle carrying both a Raman reporter for producing a signal detectable by Raman spectroscopy, and an affinity component for binding the analyte or the complex formed between the analyte and the capture agent on the diagnostic substrate.

In certain embodiments, the Raman detection agent may, optionally, further comprise other components such as, but not limited to, silica or other inert material(s) (optionally, as a coating, for example). In certain embodiments, the Raman detection agent may comprise one, or more than one Raman signal-enhancing metal nanoparticles. In certain embodiments, the Raman signal-enhancing metal nanoparticle may comprise more than one metal, for example gold and silver.

In another embodiment, there is provided herein a method for detecting the presence of an analyte in a sample from a subject or source, said method comprising:
- providing a diagnostic substrate presenting a capture agent;
- exposing the sample to a Raman detection agent, allowing analyte in the sample, if present, to bind the Raman detection agent via an affinity component presented thereon which is specific for the analyte, thereby forming an analyte-Raman detection agent complex;
- exposing the analyte-Raman detection agent complex to the diagnostic substrate, allowing the analyte-Raman detection agent complex to bind to the diagnostic substrate via the capture agent presented thereon which is specific for the analyte or the analyte-Raman detection agent complex; and
- detecting whether the Raman detection agent bound to the diagnostic substrate using Raman spectroscopy, whereby detection of Raman detection agent bound to the diagnostic substrate indicates the presence of the analyte in the sample;

wherein the Raman detection agent comprises a Raman signal-enhancing metal nanoparticle carrying both a Raman reporter for producing a signal detectable by Raman spectroscopy, and the affinity component for binding the analyte.

In yet another embodiment, there is provided herein a method for detecting the presence of an analyte in a sample from a subject or source, said method comprising:
- providing a diagnostic substrate presenting a capture agent;
- providing a Raman detection agent presenting an affinity component;
- exposing the sample simultaneously to the diagnostic substrate and the Raman detection agent, allowing the capture agent, the affinity component, and analyte in the sample, if present, to form a complex which is dependent on presence of the analyte for formation; and
- detecting whether the Raman detection agent bound to the diagnostic substrate using Raman spectroscopy, whereby detection of Raman detection agent bound to the diagnostic substrate indicates the presence of the analyte in the sample;

wherein the capture agent of the diagnostic substrate is specific for the analyte or a complex formed between the analyte and the Raman detection agent; and wherein the Raman detection agent comprises a Raman signal-enhancing metal nanoparticle carrying both a Raman reporter for producing a signal detectable by Raman spectroscopy, and the affinity component for binding the analyte or a complex formed between the analyte and the capture agent on the diagnostic substrate.

In another embodiment of the above method or methods, the diagnostic substrate may be a 3D diagnostic substrate having X, Y, and Z dimensions through which the capture agent is presented, and through which the sample may permeate when exposed thereto.

In still another embodiment of the above method or methods, the signal detectable by Raman spectroscopy may be used to quantitate the amount of analyte in the sample.

In yet another embodiment of the above method or methods, the Raman signal-enhancing metal nanoparticle may comprise a gold nanoparticle, or a silver nanoparticle.

In still another embodiment of the above method or methods, the Raman detection agent may comprise substantially monodisperse nanoparticles.

In another embodiment of the above method or methods, the nanoparticles may have an average diameter of about 13.0 nm±2.7 nm, or larger.

In still another embodiment of the above method or methods, the nanoparticles may have an average diameter of about 40 nm.

In yet another embodiment of the above method or methods, the Raman reporter may comprise malachite green, 4,4'-bipyridine, para-aminothiophenol (pATP), or Rhodamine 6G.

In another embodiment of the above method or methods, the Raman reporter may be pATP.

In still another embodiment of the above method or methods, the Raman signal-enhancing metal nanoparticle may comprise a gold nanoparticle, and the Raman reporter (for example, pATP) may be bound to the gold nanoparticle through an Au—S covalent bond.

In yet another embodiment of the above method or methods, the diagnostic substrate may comprise a nitrocellulose membrane presenting the capture agent.

In another embodiment of the above method or methods, the affinity component may comprise protein A, or an antibody or other protein capable of binding the analyte or the complex formed between the analyte and the capture agent.

In yet another embodiment of the above method or methods, the analyte may be an antibody.

In still another embodiment of the above method or methods, the capture agent may comprise an antigen derived from or related to a virus, bacteria, cancer, or other disease-related condition in a subject, or the capture agent may comprise an antibody with affinity for the analyte.

In another embodiment of the above method or methods, the Raman detection agent may further comprise a blocker for preventing non-specific binding. In certain embodiments, the blocker may comprise bovine serum albumin (BSA).

In still another embodiment of the above method or methods, the Raman spectroscopy detection step may be performed in 1080 cm$^{-1}$ mode. As will be understood, other wavelengths are possible, and the person of skill in the art, having regard to the teachings herein, will be able to select a suitable wavelength depending on the particular application and Raman reporter used.

In yet another embodiment of the above method or methods, the diagnostic substrate and the Raman detection agent may be configured, through capture agent, affinity component, and Raman reporter selection, for detecting the presence of and/or quantifying levels of more than one analyte in the sample from the subject or source.

In another embodiment, there is provided herein a Raman detection agent for detecting the presence of an analyte in a sample, the Raman detection agent comprising:
- a Raman signal-enhancing metal nanoparticle, the nanoparticle carrying both a Raman reporter for producing a signal detectable by Raman spectroscopy, and an affinity component for binding the analyte or a complex formed between the analyte and a capture agent on a diagnostic substrate.

In another embodiment of the above Raman detection agent, the Raman signal-enhancing metal nanoparticle may comprise a gold nanoparticle, the Raman reporter may comprise pATP, the affinity component may comprise protein A, the analyte may comprise an antibody, and the capture agent may comprise an antigen for the antibody.

In another embodiment, there is provided herein a method for preparing a Raman detection agent as defined hereinabove, the method comprising:
  in a first step, attaching the Raman reporter to the Raman signal-enhancing metal nanoparticle; and
  in a second step, attaching the affinity component to the Raman signal-enhancing metal nanoparticle.

In another embodiment of the above method, the method may further comprise a third step of blocking the Raman detection agent to prevent non-specific binding by exposing the Raman detection agent to a blocker.

In another embodiment, there is provided herein a kit for detecting the presence of an analyte in a sample, the kit comprising:
  a Raman detection agent as defined hereinabove, and
  one or more of a diluent, a buffer, a diagnostic substrate, a diagnostic device for housing the diagnostic substrate, a Raman spectrometer, an optional wash reagent, or a set of instructions for use of the kit in the detection of the analyte in the sample according to a method as defined hereinabove.

BRIEF DESCRIPTION OF DRAWINGS

These and other features, aspects and advantages of the present invention will become better understood with regard to the following description and accompanying drawings, wherein:

FIG. 12 shows results of analyte detection using Raman detection agents generated using Approaches A and B of FIG. 11;

DETAILED DESCRIPTION

Figure 1:
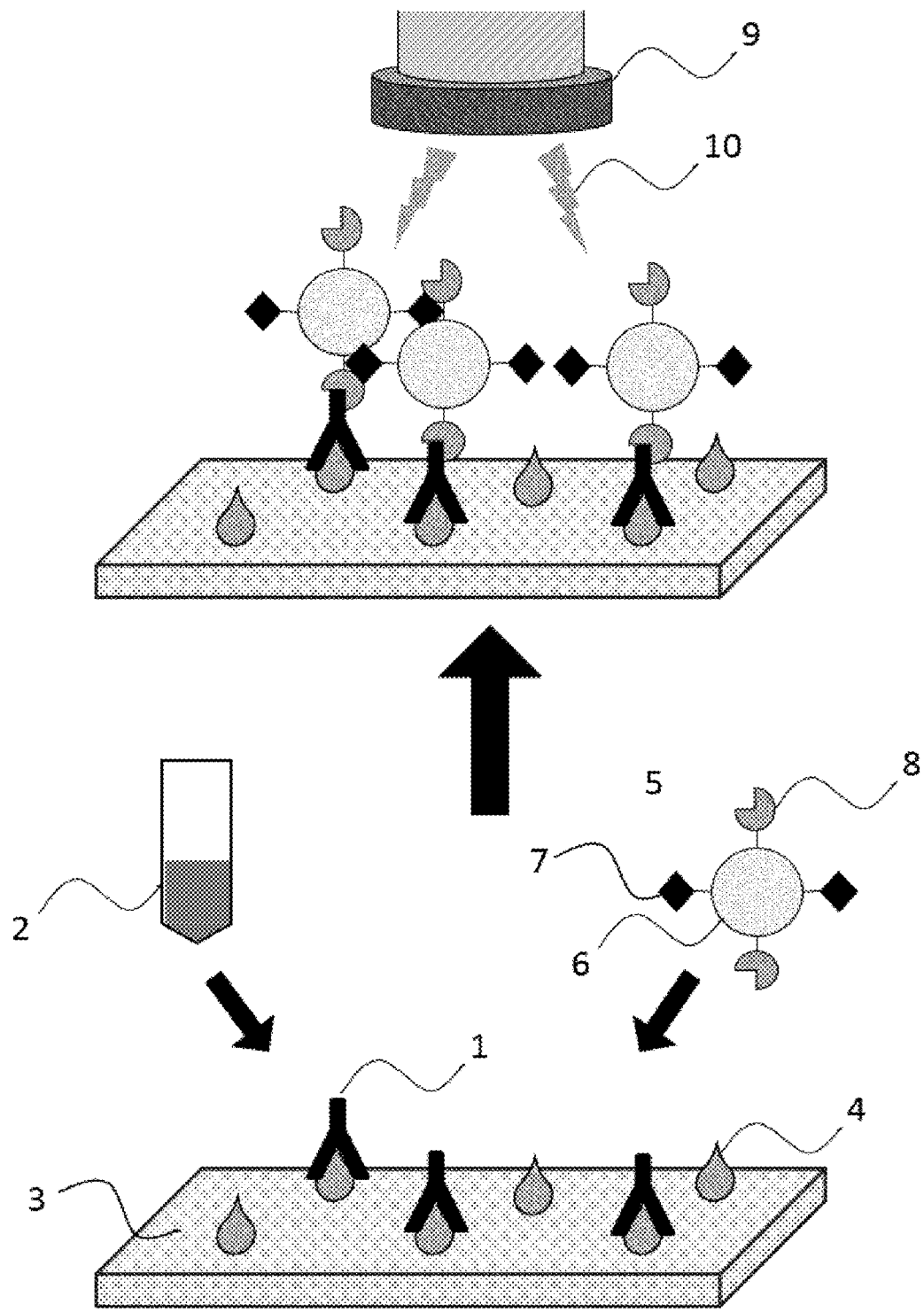
FIG. 1 shows an illustration of an embodiment of a method for detecting the presence of an analyte in a sample from a subject as described herein, which includes the use of an embodiment of a Raman detection agent as described herein as part of the method.

Described herein are methods and agents for determining the presence of an analyte in a sample using SERS Raman spectroscopy. It will be appreciated that embodiments and examples are provided herein for illustrative purposes intended for those skilled in the art, and are not meant to be limiting in any way.

In an embodiment, there is provided herein a method for detecting the presence of an analyte in a sample from a subject or source, said method comprising:
  providing a diagnostic substrate presenting a capture agent;
  exposing the sample to the diagnostic substrate, allowing analyte in the sample, if present, to bind the diagnostic substrate via the capture agent presented thereon which is specific for the analyte;
  exposing the diagnostic substrate to a Raman detection agent which binds to the diagnostic substrate via binding to the analyte, or to a complex formed between the analyte and the capture agent, if the analyte is present; and
  detecting whether the Raman detection agent bound to the diagnostic substrate using Raman spectroscopy (i.e. SERS), whereby detection of Raman detection agent bound to the diagnostic substrate indicates the presence of the analyte in the sample;

wherein the Raman detection agent comprises a Raman signal-enhancing metal nanoparticle carrying both a Raman reporter for producing a signal detectable by Raman spectroscopy, and an affinity component for binding the analyte or the complex formed between the analyte and the capture agent on the diagnostic substrate.

In another embodiment, there is provided herein a method for detecting the presence of an analyte in a sample from a subject or source, said method comprising:

providing a diagnostic substrate presenting a capture agent;

exposing the sample to a Raman detection agent, allowing analyte in the sample, if present, to bind the Raman detection agent via an affinity component presented thereon which is specific for the analyte, thereby forming an analyte-Raman detection agent complex;

exposing the analyte-Raman detection agent complex to the diagnostic substrate, allowing the analyte-Raman detection agent complex to bind to the diagnostic substrate via the capture agent presented thereon which is specific for the analyte or the analyte-Raman detection agent complex; and detecting whether the Raman detection agent bound to the diagnostic substrate using Raman spectroscopy (i.e. SERS), whereby detection of Raman detection agent bound to the diagnostic substrate indicates the presence of the analyte in the sample;

wherein the Raman detection agent comprises a Raman signal-enhancing metal nanoparticle carrying both a Raman reporter for producing a signal detectable by Raman spectroscopy, and the affinity component for binding the analyte.

In still another embodiment, there is provided herein a method for detecting the presence of an analyte in a sample from a subject or source, said method comprising:

providing a diagnostic substrate presenting a capture agent;

providing a Raman detection agent presenting an affinity component;

exposing the sample simultaneously to the diagnostic substrate and the Raman detection agent, allowing the capture agent, the affinity component, and analyte in the sample, if present, to form a complex which is dependent on presence of the analyte for formation; and detecting whether the Raman detection agent bound to the diagnostic substrate using Raman spectroscopy (i.e. SERS), whereby detection of Raman detection agent bound to the diagnostic substrate indicates the presence of the analyte in the sample;

wherein the capture agent of the diagnostic substrate is specific for the analyte or a complex formed between the analyte and the Raman detection agent; and wherein the Raman detection agent comprises a Raman signal-enhancing metal nanoparticle carrying both a Raman reporter for producing a signal detectable by Raman spectroscopy, and the affinity component for binding the analyte or a complex formed between the analyte and the capture agent on the diagnostic substrate.

In certain embodiments, the Raman detection agent may optionally further comprise other components such as, but not limited to, silica or other inert material(s) (optionally, as a coating, for example). In certain embodiments, the Raman detection agent may comprise one, or more than one Raman signal-enhancing metal nanoparticles. In certain embodiments, the Raman signal-enhancing metal nanoparticle(s) may comprise more than one metal, for example gold and silver.

As will be understood, the analyte to be detected in the sample may be any suitable analyte for which it may be desirable to determine the presence of, and/or amount of, in a sample or source, whether for medical, industrial, research, or other purposes. Samples may, for example, be those obtained from a subject, or from another source such as a source in the natural environment (i.e. water from a stream, a soil sample, etc. . . . ). Examples of analytes may include drugs, metabolites, hormones, polypeptides, proteins, polysaccharides, nucleic acids, toxins, contaminants, or other biomarkers, compounds, or molecules of either natural or synthetic origin. Analytes of interest may include those linked to, or indicative of, a viral, bacterial, cancer, or other disease-related condition or state in a subject. Analytes may also include drugs, or metabolites thereof. As well, analytes may include naturally occurring or synthetic compounds, or molecules to which a subject may be exposed and for which it may be desirable to determine whether such exposure has occurred and/or to what level the exposure has occurred.

In particular embodiments, the analyte may be an antigen, or an antibody. Antigens may include any suitable epitope-presenting compound or molecule which can be recognized by an antibody. Antibodies may include, for example, antibodies present in the subject due to prior exposure to, or infection of, the subject with a particular antigen such as a virus or bacteria (among other things). As will be understood, the presence of particular antibodies in a subject may be indicative that the subject has been exposed to the particular antigen to which the antibodies selectively bind.

Those skilled in the art will recognize that, in certain embodiments, the analyte may be any suitable small molecule (i.e. short peptide, long protein, polysaccharide, etc . . . ) of interest which may be bound to a diagnostic substrate as described herein via a capture agent immobilized thereto.

In certain embodiments, the analyte may be antibodies in the subject which target a viral or bacterial antigen. For example, the analyte may be an antibody raised by a Hepatitis C-infected subject which specifically binds a Hepatitis C virus (HCV) antigen, or an antibody raised by an HIV-infected subject which specifically binds an HIV antigen. Detection of such an analyte in a subject is, therefore, indicative that the subject has been exposed to, or infected with, HCV or HIV. The skilled person having regard to the teachings herein will be able to select a suitable analyte for a particular diagnostic application.

As will also be understood, the sample being tested may be any suitable sample suspected of containing the analyte. In certain embodiments, the sample may be a sample obtained from a subject. Samples may include, for example, a blood sample, serum sample, plasma sample, urine sample, saliva sample, or another sample obtained from the subject which is suspected of containing, or which potentially contains, the analyte. In certain embodiments, the sample may be a sample taken from the environment, such as water obtained from a lake, river, ocean or other source, or another environmental source. Samples may include those which are directly obtained, or those which are indirectly prepared (for example, swab samples of semi-solids, or solids may be extracted for subsequent exposure to the diagnostic substrate). Depending on the particular application, samples may be used directly, or first subjected to one or more upstream processing steps including, for example, centrifugation, HPLC, filtration, purification, or isolation step(s). The nature of the sample can be selected to suit a particular application. For example, for detection of blood-borne analytes, the sample may be a whole blood sample, or a processed sample obtained therefrom.

Methods described herein may include the use of diagnostic substrates upon which analyte capture and detection may occur. The person of skill in the art will be aware of many suitable diagnostic substrates, and will be able to select a diagnostic substrate to suit a particular application. In certain examples, a diagnostic substrate may comprise a nitrocellulose membrane, or another suitable surface. A diagnostic substrate may comprise one or more of glass fibers, coated glass slides, cellulose acetates, polyester, cellulose nitrate, polycarbon, nylon, carbon nanotubes, or other synthetic or natural materials, depending on the particular application. As well, in certain embodiments, a diagnostic substrate may include a 3-dimensional (3D) diagnostic substrate, at least a portion of which includes X, Y, and Z dimensions throughout which the capture agent may be presented, and throughout which the sample may permeate when exposed thereto. Such 3D diagnostic substrates may, in certain embodiments, allow for good analyte detection sensitivity and/or reproducibility.

In an embodiment, 3D diagnostic substrates may include those which allow capture agents applied thereto to permeate in X, Y, and Z dimensions, thus increasing the surface area within the diagnostic substrate on which capture agent may be immobilized for presentation. As sample is applied to such diagnostic substrates, the sample will thus be exposed in X, Y, and Z dimensions as it contacts the diagnostic substrate.

Such increased surface area of the 3D diagnostic substrate may provide increased sensitivity and/or reproducibility in certain embodiments, as compared with a corresponding 2D diagnostic substrate which does not allow Z-axis permeation. Without wishing to be bound by theory, the portion of the diagnostic substrate being assessed in 3D versus 2D may be analogous to assessing a cube versus a 2D square. In certain embodiments, penetration of capture agent beyond the upper surface of the diagnostic substrate, (i.e., in certain embodiments, to a Z-axis depth greater than about 5 microns) may facilitate reproducibility, as the capture agent may be immobilized within the diagnostic substrate which the analyte is traveling through, rather than simply being present on the interface between the diagnostic substrate and the physical layer immediately above the diagnostic substrate.

Crawford et al. (DOI: 10.1021/acs.analchem.6b01263; 2016, Anal. Chem. 88(12):6515-6522) has recently studied reactions occurring on a two dimensional substrate using Raman scattering. In their studies, the effect of sampling a larger surface, albeit in two dimensions, increased sensitivity and reproducibility. Others have also taken a similar approach; Choi assessed a larger surface in the x and y dimension in a grid approach (Choi et al (DOI: 10.1016/j.snb.2016.08.178); 2016; 240:358-364). Choi et al assessed a surface measuring 200 µm×1500 µm surface using a computer controlled x-y translational stage in 10 µm by 10 µm steps in order to collect data across the surface. In contrast, 3D diagnostic substrates described herein place increased surface area in the z-dimension. By assessing surface area within a third dimension, the need for specialized equipment may also be reduced. Both aforementioned approaches use specialized equipment, i.e. lasers which illuminate larger spots, or use translational stages to scan larger surface area. Use of 3D diagnostic substrates as described herein may reduce the use of specialized equipment, and/or may decrease substrate assessment time while, and/or may increase sensitivity and/or reproducibility.

For analysis via Raman spectroscopy, the diagnostic substrate may be chosen so as to have a Raman spectra or profile in the region(s) relevant to detection of the Raman reporter which does not substantially interfere with or confound detection of the Raman reporter. In certain embodiments, the diagnostic substrate itself may provide a Raman signal which may be used as an internal control during Raman spectroscopy analysis, or the diagnostic substrate may include an internal standard component which produces a Raman signal useful as an internal control, or both.

The diagnostic substrate may also be chosen so as to provide a suitable porosity and/or Wicking power to allow for suitable flow rate and/or assay sensitivity for a particular application. A variety of diagnostic substrate examples are described in U.S. Pat. No. 8,025,850, for example, the entirety of which is herein incorporated by reference.

As will be understood, in certain embodiments, diagnostic substrates may include one or more layers (which may be the same, or different from one another), and may comprise permeable, porous, or fibrous material(s) to which the sample may be exposed, or through which the samples may be passed. In certain examples, diagnostic substrates may be absorbent, and/or may allow sample diffusion therethrough via diffusion, osmosis, capillary action, gravity action, or another suitable active or passive mechanism.

Diagnostic substrates may present one or more capture agents, which are capable of capturing the analyte (which may, in certain embodiments, be complexed with the Raman detection agent) when exposed thereto. The diagnostic substrates may be derivatized or otherwise functionalized by the one or more capture agents such that the capture agents are able to encounter the analyte, and retain the analyte at the diagnostic substrate. Capture agents may be joined with, or immobilized on, the diagnostic substrates via, for example, covalent bonding, non-covalent (i.e. electrostatic, hydrophobic, or Van der Waals) interactions, or both.

In certain embodiments in which the diagnostic substrate is a 3D diagnostic substrate, the 3D nature of the diagnostic substrate may allow for capture agent(s) to permeate into the diagnostic substrate in all three dimensions. By way of example, capture agents contained in solution may be applied to the 3D diagnostic substrate by placing the 3D diagnostic substrate on an appropriate surface and then spraying, dispensing droplets of, or otherwise physically applying a solution containing the capture agent onto the 3D diagnostic substrate from above or below. Once dispensed, capture agent(s) to be applied to the 3D diagnostic substrate may be dispersed in both the X and Y axis, and may also penetrate within the Z axis. Such penetration may allow the capture agent(s) to traverse into the 3D diagnostic substrate such that they may be embedded within the substrate, rather than just positioning on top of it. Such permeation may effectively increase the surface area of the 3D diagnostic substrate which contains capture agent with which analyte applied thereto may interact as the analyte moves through the diagnostic substrate. Penetration into the Z-axis may, for example, occur by passive absorption of the solution/sample, or it may be assisted by motive force such as the application of a vacuum to draw capture reagent and/or sample into the Z-axis after the solution/sample contacts the 3D diagnostic substrate in the X and Y axes. The volume of solution containing the capture reagent, and the concentration of capture reagent within the solution, may be further selected so as to provide a suitable or desired sensitivity and/or reproducibility, for example.

The person of skill in the art will be able to select a suitable capture agent depending on the particular application. A capture agent may include any suitable agent capable of recognizing and binding to a particular analyte (or analyte complex) to be detected under the conditions of the assay. The capture agent may be selected so as to be selective for binding to the analyte or analyte complex. Where the analyte is, for example, an antibody specific for a particular antigen, the capture agent may be the particular antigen, or another agent which presents one or more epitopes of the antigen. Capture agents may include antibodies or receptors capable of binding to a particular analyte, or a particular class or group of analytes, depending on the particular application. As well, capture agents may, in certain embodiments, include natural or synthetic antibodies, antigen-binding fragments thereof, receptors, antigens, enzymes, lectins, nucleic acids, avidin, protein A, and the like, depending on the particular application. A variety of capture agent options are described in U.S. Pat. No. 8,025,850, for example, the entirety of which is herein incorporated by reference.

It will be understood that, in certain embodiments, more than one capture agent may be used. The capture agents may be specific for the same analyte, or for different analytes. Where capture agents bind to different analytes, each analyte may be indicative of the same disease, condition, or state, or may be indicative of different diseases, conditions, or states, for example. Thus, by using a plurality of capture agents directed toward different analytes, certain embodiments of methods as described herein may allow for concurrent detection of more than one analyte present within the sample. In certain embodiments, different capture agents (which may be directed toward the same analyte, or toward different analytes) may be localized to distinct regions of the diagnostic substrate in order to facilitate sample analysis and diagnostic read-out.

As will be understood, diagnostic substrates (and capture agents present thereon) and/or Raman detection agents (and affinity components and/or Raman reporters presented thereon) may be selected so as to allow for detection of more than one analyte concurrently. The skilled person having regard to the teachings herein will be able to configure such elements for detecting the presence of and/or quantifying the levels of more than one analyte in the sample in a fashion which is appropriate for the particular application of interest.

In certain embodiments, the diagnostic substrates may be pre-treated with a blocking composition prior to use, where the blocking composition prevents non-specific binding of components present in the sample to the diagnostic substrate. Common blocking solutions include bovine serum albumin (BSA)-based solutions, or other proteins, molecules, or chemical compounds, which do not interfere with, or cross-react with, components of the particular assay. In examples where non-specific binding is not problematic, or where the diagnostic substrate is chosen so as to substantially avoid non-specific binding, such blocking treatment may be unnecessary, or optional.

As will be understood, methods as described herein may include a step of exposing the sample to the diagnostic substrate which presents the capture agent. In certain embodiments, exposure of the sample to the diagnostic substrate may be followed by one or more washing steps to remove non-analyte components of the sample. Such washing(s) may be optional, and employed as is suitable for the particular application. Such exposure steps may be performed using any suitable technique which is appropriate for the particular diagnostic application and set-up being used. The diagnostic substrate may form part of a flow-through, vertical-flow, or lateral-flow or strip test diagnostic apparatus, for example, and the exposure of the sample may be performed in accordance with the particular set-up design.

In certain embodiments, the sample may be exposed to the diagnostic substrate directly, or the sample may be filtered and/or purified and/or subjected to other upstream processing steps prior to exposure to the diagnostic substrate. In certain embodiments, the sample may be exposed to the Raman detection agent so as to form analyte-Raman detection agent complexes prior to exposure to the diagnostic substrate. In certain embodiments, the sample may be concentrated prior to introduction to the diagnostic substrate, or may be diluted by a diluent or buffer or other reagent prior to introduction. The sample may be introduced to the diagnostic substrate all at once or gradually, and may be applied by a user or by a sample application unit designed to apply the sample in an automated or manual fashion. The sample may be introduced by flowing the sample through or over the diagnostic substrate, or allowed to diffuse into the diagnostic substrate, for example. In certain embodiments, the sample may be dropped, pressed, or rubbed onto the diagnostic substrate. The skilled person having regard to the teachings herein will be able to select a suitable exposure technique to suit a particular diagnostic application, and is not limited to those exemplified above.

The manner in which the sample is exposed to the diagnostic substrate may simply be selected to suit the particular diagnostic device and set-up being used, so long as the exposure results in binding of the analyte to the capture agent presented on the diagnostic substrate. The nature of the binding between the analyte and the capture agent will depend on the particular analyte/capture agent pair being used, and will typically involve non-covalent binding (through electrostatic, hydrophobic, and/or Van der waals interaction(s), for example), although covalent binding may also be possible in certain examples.

Following exposure of the sample to the diagnostic substrate and binding of the analyte (if present in the sample) to the capture agent, the diagnostic substrate may then be exposed to a Raman detection agent. In other embodiments, the sample may be exposed to the Raman detection agent so as to form an analyte-Raman detection agent complex, which may then be exposed to the diagnostic substrate. In still other embodiments, the sample may be exposed substantially simultaneously to both the Raman detection agent and the diagnostic substrate. The Raman detection agent may be any suitable agent which comprises:
- a Raman signal-enhancing metal nanoparticle;
- a Raman reporter carried by the nanoparticle, the Raman reporter being for producing a signal detectable by Raman spectroscopy; and
- an affinity component carried by the nanoparticle, the affinity component being for binding to the analyte, or a complex formed between the analyte and a capture agent, on the diagnostic substrate.

As will be understood, the Raman detection agent may be any suitable agent which is able to recognize and bind to the analyte (either before or after the analyte binds to the capture agent), or a complex formed between the analyte and a capture agent on the diagnostic substrate, and provide a signal detectable by Raman spectroscopy.

In certain embodiments, the Raman detection agent may take advantage of surface-enhanced Raman spectroscopy (SERS) effects, thus providing detection sensitivity. In such embodiments, the Raman detection agent may comprise a Raman signal-enhancing metal nanoparticle or colloidal particle which contributes a Raman enhancement effect.

SERS effects are described in further detail in D. L. Jeanmaire and R. P. Van Duyne, *J. Electroanal. Chem.*, 84, 1-20 (1977) and M. G. Albrecht and J. A. Creighton, *J. Am. Chem. Soc.*, 99, 5215-5217, both of which are herein incorporated by reference in their entirety. The Raman signal-enhancing metal nanoparticle may thus comprise a gold nanoparticle (AuNP), or a silver nanoparticle (AgNP), although other nanoparticles may be possible such as copper, platinum, or palladium nanoparticles in certain examples. U.S. Pat. No. 8,025,850 provides examples of colloidal gold particles and the preparation thereof.

In certain embodiments, the Raman detection agent may comprise substantially monodisperse Raman signal-enhancing metal nanoparticles. For example, the nanoparticles may have an average diameter of about 13.0 nm±2.7 nm, or larger. In certain embodiments, the nanoparticles may have an average diameter of about 40 nm, for example.

Raman reporters carried on the Raman signal-enhancing nanoparticle may include any suitable Raman reporter which can be joined to the Raman signal-enhancing nanoparticle and which can provide a signal detectable by Raman spectroscopic analysis once the Raman detection agent has bound to the analyte, or a complex formed between the analyte and a capture agent, on the diagnostic substrate. Raman reporters may include any suitable Raman reporter compound or molecule known to the person of skill in the art having regard to the teachings herein, and may be selectable by the skilled person to suit a particular application as needed. Raman reporters may be selected so as to provide a detectable Raman signal which is not impaired, interfered with, or masked, by the Raman spectra of the diagnostic substrate and other components of the methods and assays described herein. Examples of suitable Raman reporters may include malachite green, 4,4'-bipyridine, para-aminothiophenol (pATP), and Rhodamine 6G, although other Raman reporters are also possible and contemplated herein.

It will be understood that Raman detection agents as described herein may include one, or more than one, Raman reporter(s). For example, two or more Raman reporters may be used in the same Raman detection agent, thereby providing multiple signals for detection by Raman spectroscopy. In certain embodiments, two or more distinct Raman reporters may be used, which may each be attached to the same Raman signal-enhancing metal nanoparticle or colloid. In certain other embodiments, two or more distinct Raman detection agents, each featuring a different Raman reporter, may be used in a homologous mixture which may include substantially equivalent amounts of the different Raman detection agents, or particular ratios between different Raman detection agents, for example.

Raman reporters may be carried on, or joined to, the Raman signal-enhancing nanoparticles by any suitable method or technique known to the person of skill in the art. For example, Raman reporters may be covalently joined to the nanoparticles, or non-covalently joined to the nanoparticles (via, for example, electrostatic, hydrophobic, and/or Van der waals interactions). Attachment may be direct (for example, by covalent Au—S bonding or by non-covalent electrostatic association), or may be indirect (mediated via, for example, biotin-avidin interaction).

Affinity components carried on the Raman signal-enhancing nanoparticle may include any suitable affinity component which can be joined to the Raman signal-enhancing nanoparticle and which can bind to the analyte, or the complex formed between the analyte and the capture agent, on the diagnostic substrate. Suitable affinity components include those which are capable of specifically binding to the analyte, or to a bivalent complex formed between the analyte and the capture agent, when exposed thereto.

The person of skill in the art will be able to select a suitable affinity component depending on the particular application. An affinity component may include any suitable agent capable of recognizing and binding to a particular analyte to be detected, or the complex formed between the analyte and the capture agent, under the conditions of the assay. The affinity component may be selected so as to be selective for binding to the analyte, or to the complex formed between the analyte and the capture agent. Where the analyte is, for example, an antibody specific for a particular antigen, the affinity component may be an anti-antibody antibody or an antigen-binding fragment (Fab) thereof, an antibody-binding protein, the particular antigen, or another agent which presents one or more epitopes of the antigen, depending on the nature of the analyte and the capture agent being used. Affinity components may include antibodies or receptors capable of binding to a particular analyte, or a particular class or group of analytes, or complexes formed between the analyte and the capture agent, depending on the particular application. As well, affinity components may, in certain embodiments, include natural or synthetic antibodies, antigen-binding fragments thereof, receptors, antigens, enzymes, lectins, nucleic acids, avidin, protein A, and the like, depending on the particular application. A variety of affinity component options are described in U.S. Pat. No. 8,025,850, for example, the entirety of which is herein incorporated by reference.

It will be understood that, in certain embodiments, more than one affinity component may be used. The affinity components may be specific for the same analyte or analyte/capture agent complex target, or for different analyte or analyte/capture agent complex targets. Where affinity components bind to different targets, each target may be indicative of the same disease, condition, or state, or may be indicative of different diseases, conditions, or states. Thus, by using a plurality of affinity components directed toward different analytes, certain embodiments of methods as described herein may allow for concurrent detection of more than one analyte present within the sample.

In embodiments where more than one capture agent is used for concurrently detecting more than one analyte in the sample, Raman detection agent(s) may be selected accordingly so as to provide the desired detection. Where two or more analytes are to be detected, for example, a corresponding number of distinct Raman detection agents may be used, each carrying a distinct and distinguishable Raman reporter paired on the nanoparticle with a distinct affinity component specific for one of the analytes to be detected. Alternatively, the Raman detection agent may carry a plurality of affinity components allowing the same Raman detection agent to detect a plurality of different analytes. The skilled person having regard to the teachings herein will understand that a variety of different capture agent(s)/analyte(s)/affinity component(s)/Raman reporter(s) combinations may be possible, and will be able to select a suitable combination for a particular application.

In certain embodiments, the Raman detection agent may further comprise a blocker for preventing non-specific binding to components other than the analyte and/or the analyte/capture agent complex. The blocker may be, for example, bovine serum albumin (BSA) or other protein(s) which do not interfere with, or cross-react with, components of the particular assay. In examples where non-specific binding is not problematic, such a blocker may be unnecessary, or optional.

As will be appreciated, in certain embodiments the combination of capture agent, analyte, and affinity component may take the form of a sandwich-type interaction, forming a 3-membered complex with the analyte captured between the capture agent and the affinity component. Where the analyte is an antibody, the capture agent may be an antigen to which the antibody binds and the affinity component may be protein A, or an anti-antibody antibody such as an anti-IgG antibody. Where the analyte is a protein or other biomarker, both the capture agent and the affinity component may be antibodies or receptors specific for different regions of the protein or biomarker such that a 3-membered complex can form therebetween. The skilled person will be aware of various specific binding member pairs which are amenable for use in methods and assays as described herein.

As will also be appreciated, in certain embodiments the combination of capture agent, analyte, and affinity component may take the form of a competitive-type interaction, wherein capture of the analyte by the capture agent can prevent or reduce binding between the affinity component and the capture agent which would otherwise occur in the absence of the analyte. In such cases, an absence or reduction of signal detection of the Raman reporter indicates presence of the analyte in the sample. Where the analyte is an antibody, the capture agent may be an antigen to which the antibody binds and the affinity component may be another antibody which binds to the capture agent with an affinity which is not sufficient to significantly displace the analyte, for example. Thus, although the affinity component as described herein typically has affinity for binding to the analyte, or a complex formed between the analyte and the capture agent, on the diagnostic substrate, it is also contemplated that the affinity component may be selected to have affinity for binding to the capture agent while the capture agent is in an unbound state free of the analyte. The skilled person will be aware of various specific binding member pairs which are amenable for use in methods and assays as described herein.

The manner in which the Raman detection agent is exposed to the diagnostic substrate (or, in certain embodiments, the sample) may be similar to that used to expose the sample to the diagnostic substrate, or may be a different manner. Such exposure may be performed using any suitable technique which is appropriate for the particular diagnostic application and set-up being used. The diagnostic substrate may form part of a flow-through, vertical-flow, or lateral-flow diagnostic apparatus, for example, and the exposure of the Raman detection agent may be performed in accordance with the particular set-up design.

In certain embodiments, the Raman detection agent may be exposed to the diagnostic substrate directly, or the Raman detection agent may first be reconstituted or otherwise processed, activated, or manipulated prior to exposure to the diagnostic substrate. The Raman detection agent may be concentrated prior to introduction to the diagnostic substrate, or may be diluted by a diluent or buffer or other reagent prior to introduction. The Raman detection agent may be introduced to the diagnostic substrate all at once or gradually, and may be applied by a user or by a reagent application unit designed to apply the Raman detection agent in an automated or manual fashion. The Raman detection agent may be introduced by flowing the Raman detection agent through or over the diagnostic substrate, or allowed to diffuse into the diagnostic substrate, for example. In certain embodiments, the Raman detection agent may be dropped, pressed, or rubbed onto the diagnostic substrate. The skilled person having regard to the teachings herein will be able to select a suitable exposure technique to suit a particular diagnostic application, and is not limited to those exemplified above.

In certain embodiments, the Raman detection agent may be mixed with the sample prior to exposure to the diagnostic substrate, and may include formation of an analyte-Raman detection agent complex. Such a mixture may, in certain embodiments, then be exposed to the diagnostic substrate directly, or otherwise processed, activated, or manipulated prior to exposure to the diagnostic substrate. Exposure may be all at once or gradually, and may be applied by a user or by a reagent application unit designed to apply the mixture in an automated or manual fashion. The mixture may be introduced by flowing it through or over the diagnostic substrate, or allowed to diffuse into the diagnostic substrate, for example. In certain embodiments, the mixture may be dropped, pressed, or rubbed onto the diagnostic substrate. The skilled person having regard to the teachings herein will be able to select a suitable exposure technique and is not limited to those exemplified above.

The manner in which the Raman detection agent is exposed to the diagnostic substrate may simply be selected to suit the particular diagnostic device and set-up being used, so long as the exposure results in binding of the Raman detection agent to the analyte, or to a complex formed between the analyte and the capture agent, immobilizing the Raman detection agent on the diagnostic substrate via the affinity component. The nature of the binding will depend on the particular analyte/affinity component/capture agent pairs being used, and will typically involve non-covalent binding (through electrostatic, hydrophobic, and/or Van der waals interaction(s), for example), although covalent binding may also be possible in certain examples. As will be understood, in certain embodiments, the Raman detection agent does not bind to the diagnostic substrate in the absence of the target analyte. In certain embodiments, the Raman detection agent is exposed to the diagnostic substrate after the sample has already been exposed thereto. In certain other embodiments, the Raman detection agent is exposed to the sample, thereby forming an analyte-Raman detection agent complex, which binds to the diagnostic substrate via the capture agent.

Examples of suitable diagnostic devices adaptable to methods described herein, and to which the diagnostic substrate described herein may be paired or housed, include those described in U.S. Pat. No. 8,025,850 and US Patent Publication No. US2011/0256638, both of which are herein incorporated by reference in their entirety.

In certain embodiments, a diagnostic device adaptable to methods described herein, and to which the diagnostic substrate described herein may be paired, may comprise a downward or vertical flow-through rapid diagnostic device as described in, for example, US Patent Publication No. US2011/0256638A1. Such devices may comprise a test area and a reagent storage area, which may be linked via a channel. The test area may comprise the diagnostic substrate, which may comprise a reaction zone and an absorbent zone, where the capture agent is immobilized on the reaction zone to detect the analyte in a fluid test sample. The sample may flow downward or vertically through the reaction zone and into the absorbent zone, with the capture agent and the analyte forming a two-membered complex that is concentrated in the reaction zone. The reagent storage area of the device may comprise a breakable cartridge positioned directly and vertically above the test area and a channel. A reagent used in the assay may be housed in the breakable cartridge. Once liberated, the reagent may pass through the channel and flow to test area for depositing on the reaction zone. When used in connection with a method as described herein, the reagent stored in the reagent storage area may comprise, for example, a Raman detection agent as described herein. Alternatively, or in addition, the reagent storage area may comprise a reagent which can suspend/reconstitute and carry a Raman detection agent, stored between the breakable cartridge and the test area, to the test area.

In certain alternative embodiments, a diagnostic device adaptable to methods described herein, and to which the diagnostic substrate described herein may be paired, may include a flow-through rapid diagnostic device as described in, for example, U.S. Pat. No. 8,025,850. Such devices may comprise a test unit and an indicator reagent delivery unit, capable of receiving a fluid sample and a buffer, respectively. The test unit may comprise the diagnostic substrate described herein, which may comprise a reaction zone containing immobilized capture agent that can specifically bind to the analyte, an absorbent zone supporting the reaction zone, and optionally, a blood separation zone in lateral fluid communication with the reaction zone. The indicator reagent delivery unit may comprise an indicator reagent capable of being placed in fluid communication with the reaction zone of the test unit. When used in connection with a method as described herein, the indicator reagent delivery unit may comprise, for example, a Raman detection agent as described herein. Alternatively, or in addition, the indicator reagent delivery unit may comprise a reagent which can suspend/reconstitute and carry a Raman detection agent as described herein to the test area.

The skilled person having regard to the teachings provided herein will be aware of many suitable diagnostic devices and set-ups which may be adaptable for use in methods as described herein, and is not limited to those described hereinabove. Furthermore, the manner in which the sample and the Raman detection agent are exposed to the diagnostic substrate may simply be selected to suit the particular diagnostic device and set-up being used, so long as the exposures result in binding of the analyte (or an analyte-Raman detection agent complex) to the capture agent presented on the diagnostic substrate, and binding of the Raman detection agent to the analyte (or to a complex formed between the analyte and the capture agent), immobilized on the diagnostic substrate.

Once the diagnostic substrate has been exposed to both the sample and the Raman detection agent, or to a mixture of the sample and the Raman detection agent, as described hereinabove, one or more washing steps may be performed to remove unbound Raman detection agent. Such washing(s) may be optional, and employed as is suitable for the particular application. After the one or more washing(s) have been performed (or skipped, where the washing(s) are optional or unnecessary), the diagnostic substrate may be analyzed by Raman spectroscopy to detect whether or not the Raman detection agent is bound thereto and/or the quantity of Raman detection agent bound thereto, thereby detecting the presence or absence of the analyte in the sample and/or the quantity of analyte in the sample. The Raman spectroscopic analysis may involve acquiring one or more Raman spectra of the diagnostic substrate using a suitable Raman spectrometer and a suitable experimental technique for the Raman reporter and other assay components being used, and analyzing the one or more acquired Raman spectra to determine the presence of and/or intensity of Raman reporter signal observed from the diagnostic substrate. In certain embodiments, the Raman spectroscopy detection step may be performed in 1080 $cm^{-1}$ mode, for example. One or more internal controls may be used to provide a baseline, or to provide a calibration point or curve, to assist in assessment of the Raman reporter signal.

Results of the Raman spectroscopy analysis may subsequently be used to diagnose, or facilitate diagnosis, of the subject from which the sample was obtained. Qualitative results concerning the presence or absence of the analyte in the sample may be used to, for example, determine whether a subject has, or has been exposed to, a particular pathogen. Quantitative results concerning the amount of analyte present in the sample may be used to, for example, assess the severity of a particular disease or condition in the subject, optionally through comparison with quantitative data obtained from one healthy subjects, one or more affected subjects, or from a sample obtained from the subject being diagnosed at an earlier point in time, for example. The skilled person having regard to the teachings provided herein will be able to arrive at the appropriate diagnosis based on the qualitative or quantitative results of the Raman spectroscopic analysis while considering the nature of the analyte being detected, and the nature of the diagnostic substrate and Raman detection agent being used.

In certain embodiments, the sample applied to the diagnostic substrate may be obtained by sampling environmental or industrial surfaces or environments. Qualitative results concerning the presence or absence of the analyte in the sample may be used to, for example, determine whether an environmental or industrial surface has been exposed to a particular substance, or to determine if a substance which typically is in contact with the surface has been removed from it by a previously completed cleaning procedure, for example. Quantitative results concerning the amount of analyte present in the sample may be used to, for example, assess the levels of contaminants present on a surface or in an environment, for example. The skilled person having regard to the teachings provided herein will be recognize appropriate conclusions based on the qualitative or quantitative results of Raman spectroscopic analysis while considering the nature of the analyte being detected, and the nature of the diagnostic substrate and Raman detection agent being used.

In yet another embodiment, there is provided herein a method for preparing a Raman detection agent as described hereinabove, the method comprising:

in a first step, attaching the Raman reporter to the Raman signal-enhancing metal nanoparticle; and in a second step, attaching the affinity component to the Raman signal-enhancing metal nanoparticle.

It will be understood that, in certain embodiments, the order of the first and second steps may be reversed. However, in at least some examples, performing the first step before the second step may be desirable for obtaining Raman detection agents providing beneficial SERS effect allowing for analysis by Raman spectroscopy.

In certain further embodiments, the method for preparing a Raman detection agent may further comprise a third step of blocking the Raman detection agent to prevent non-specific binding to components other than the analyte and/or the analyte/capture agent complex by exposing the Raman detection agent to a blocker such as, for example, bovine serum albumin (BSA) or other protein(s) which do not interfere with, or cross-react with, components of the particular assay. In examples where non-specific binding is not problematic, such a third step of blocking may be unnecessary, or optional.

In yet another embodiment, there is provided herein a kit, such as an assay kit, for detecting the presence of an analyte in a sample (such as, for example, a sample from a subject or other source) according to a method as defined hereinabove, the kit comprising:

a Raman detection agent as described hereinabove, and one or more of a buffer, a diagnostic substrate, a diagnostic device for housing the diagnostic substrate, a Raman spectrometer, or an optional wash reagent as described hereinabove, or a set of instructions for use of the kit in the detection of the analyte in the sample according to a method as defined hereinabove.

In certain embodiments, kits may be provided which include a Raman detection agent as described hereinabove, and a diagnostic substrate as described hereinabove which is optionally housed in a suitable diagnostic device which may allow or facilitate exposure of the diagnostic substrate to the sample, the Raman detection agent, or both. Examples of suitable diagnostic devices for inclusion in such kits have been described herein, and may include those described in U.S. Pat. No. 8,025,850 and US Patent Publication No. US2011/0256638 (both of which are herein incorporated by reference in their entirety) which have been adapted for use in methods as described herein.

Kits may be provided to specifically allow for detection of a particular analyte in a sample according to the needs of the end user. For example, an HCV kit may be provided which includes a diagnostic substrate presenting a capture agent which is an HCV antigen, and a Raman detection agent carrying an affinity component which is specific for binding to an anti-HCV antibody. Alternatively, a kit for HIV detection might include a diagnostic substrate presenting a capture agent which is an HIV antigen, and a Raman detection agent carrying an affinity component which is specific for binding to an anti-HIV antibody.

Several examples will now be provided to further illustrate certain methods and agents for determining the presence of an analyte in a sample using Raman spectroscopy as are described in detail herein. It will be appreciated that the following examples are provided herein for illustrative purposes intended for those skilled in the art, and are not meant to be limiting in any way.

Example 1

Method and Detection Agent for the Detection of HCV Antibody in a Sample from a Subject An example of a method for detecting the presence of an analyte in a sample from a subject as described herein is graphically depicted in FIG. 1. This illustrative method example includes the use of an example of a Raman detection agent as described herein as part of the depicted method.

FIG. 1 illustrates an embodiment of method for detecting the presence of an analyte (1) in a sample (2) from a subject, said method comprising:

providing a diagnostic substrate (3) presenting a capture agent (4) for the analyte (1);
exposing the sample (2) to the diagnostic substrate (3), allowing analyte (1) in the sample (2) to bind to the capture agent (4) presented thereon;
exposing the diagnostic substrate (3) to a Raman detection agent (5) which binds to the diagnostic substrate via binding to the analyte (1), or to a complex formed between the analyte (1) and the capture agent (4); and
detecting the Raman detection agent (5) bound to the diagnostic substrate (3) by Raman spectroscopy, thereby detecting the presence of the analyte (1) in the sample (2);

wherein the Raman detection agent (5) comprises a Raman signal-enhancing metal nanoparticle (6) carrying both a Raman reporter (7) for producing a signal detectable by Raman spectroscopy, and an affinity component (8) for binding to the analyte (1) or the complex formed between the analyte (1) and the capture agent (4) on the diagnostic substrate (3).

Once both the sample (2) and the Raman detection agent (5) have been exposed to the diagnostic substrate (3), the presence of the Raman reporter (7) is detected on the diagnostic substrate (3) using a Raman spectrometer (9). In this example, the Raman detection agent (5) includes a Raman signal-enhancing metal nanoparticle (6) which promotes a SERS signal enhancement effect (10), which may provide for detection with good sensitivity.

The illustrated method is being used to detect the presence of HCV antibodies in the sample (2). Thus, the sample (2) is a blood sample from the subject, and the analyte (1) is an HCV-specific antibody. The diagnostic substrate (3) is a 3D nitrocellulose membrane presenting immobilized HCV antigen as capture agent (4). Once exposed thereto, the analyte (1) binds to the capture agent (4), forming an antigen/capture agent complex. The Raman detection agent (5) used in this example comprises a Raman signal-enhancing metal nanoparticle (6) which is a gold nanoparticle (AuNP), which carries a Raman reporter (7) which is pATP and an affinity component (8) which is protein A capable of binding the HCV-specific antibody. Once exposed thereto, the Raman detection agent (5) binds to the antigen (1) portion of the antigen/capture agent complex formed in the previous step. The Raman reporter (7) is then detected by Raman spectroscopy using a Raman spectrometer (9) operating in 1080 $cm^{-1}$ mode, thereby providing for detection with good sensitivity due to the SERS effect (9) of the AuNP.

Figure 17:
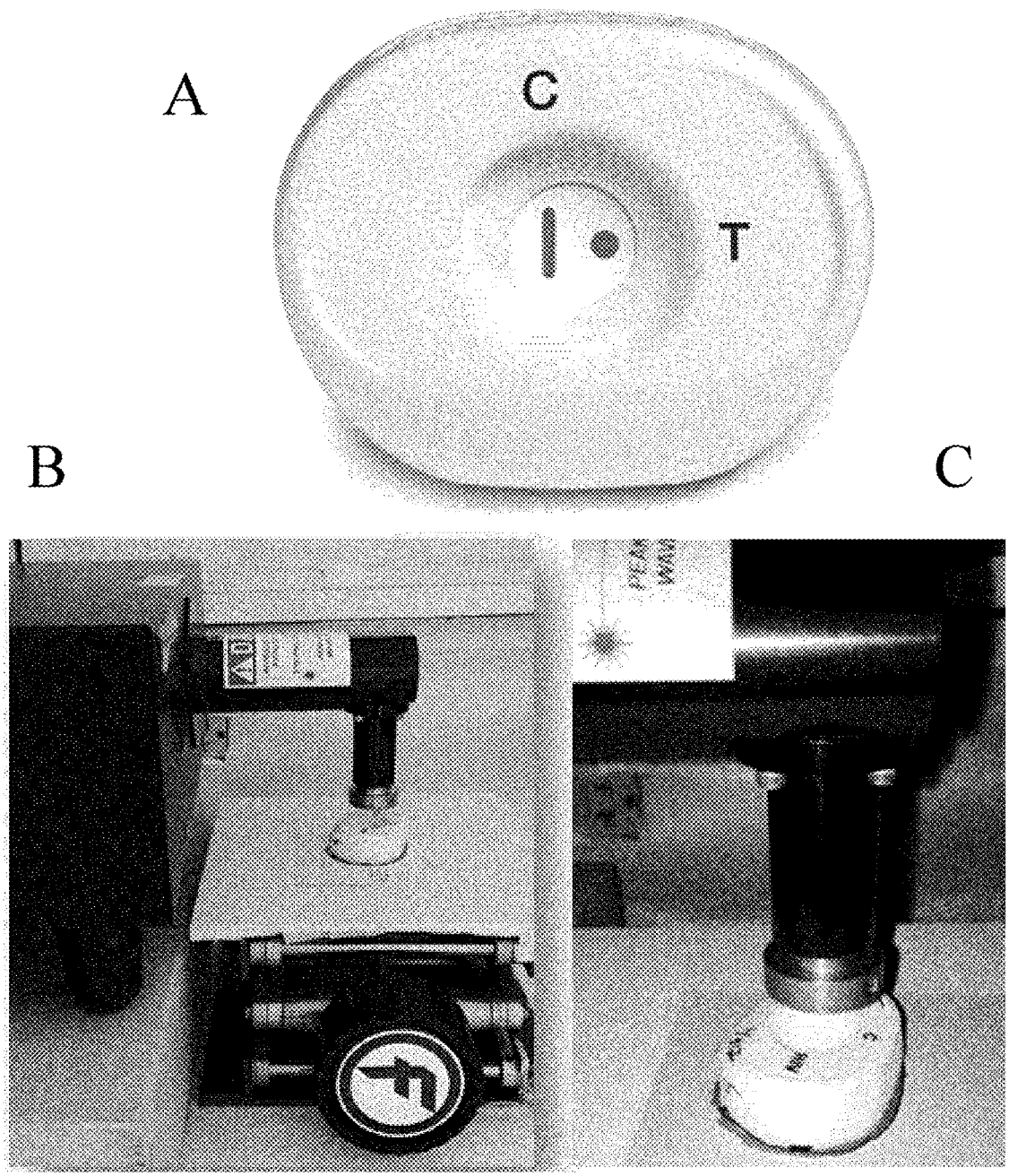
FIG. 17 shows photographs of a diagnostic substrate as described herein, mounted in a diagnostic device (A), and being analyzed by Raman spectroscopy ((B) and (C))

FIG. 17 shows photographs of a diagnostic substrate such as that described in this example, mounted in a diagnostic device (A), and being analyzed by Raman spectroscopy ((B) and (C)).

Example 2

Raman Reporter Selection

Raman detection agents as described herein comprise a Raman reporter, which may be joined to a Raman signal-enhancing nanoparticle. The Raman reporter may be selected so as to provide a signal detectable by Raman spectroscopic analysis once the Raman detection agent has bound to the analyte, or a complex formed between the analyte and a capture agent, on the diagnostic substrate.

Figure 2:
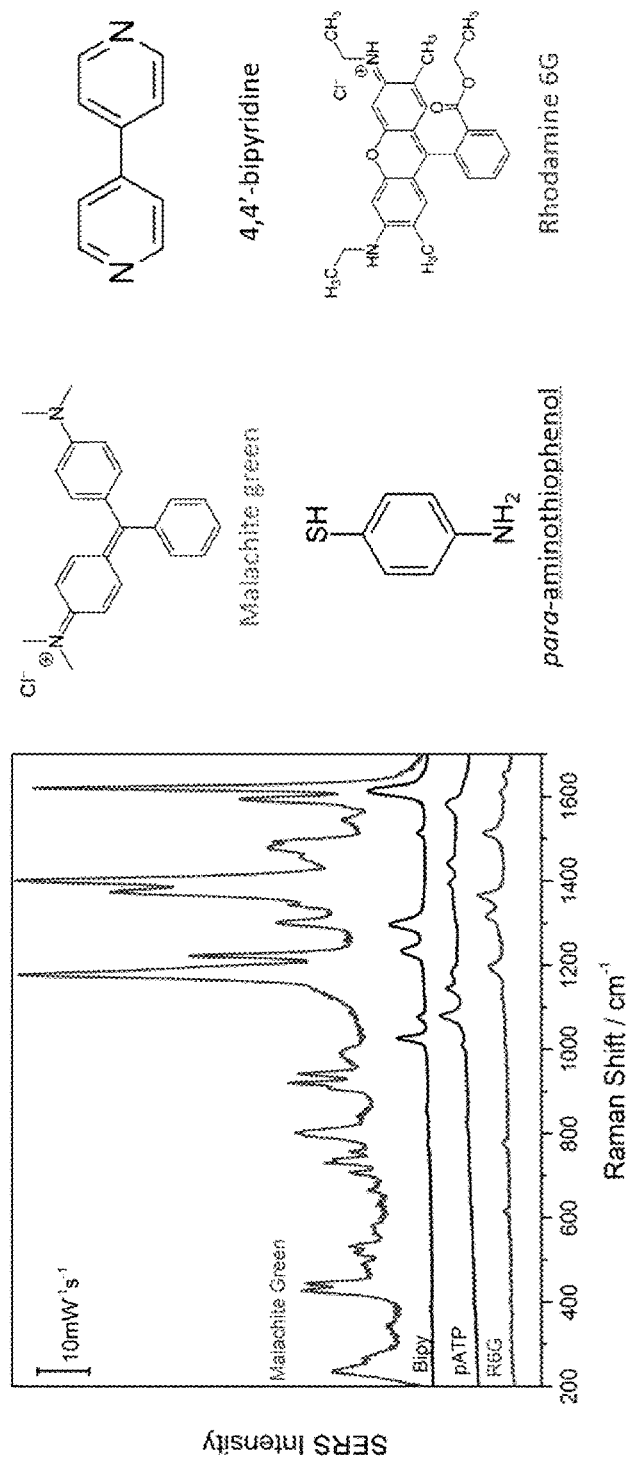
FIG. 2 shows Raman spectra obtained for four different Raman reporter molecules.

FIG. 2 provides Raman spectra obtained for a set of Raman reporters which includes malachite green, 4,4'-bipyridine, para-aminothiophenol (pATP), and Rhodamine 6G. Such Raman spectra may be useful when selecting a Raman reporter to suit a particular application, as the Raman reporters may be chosen so as to provide a detectable Raman signal which is not impaired, interfered with, or masked, by the Raman spectra of the diagnostic substrate and other components of the methods and assays described herein.

Figure 3:
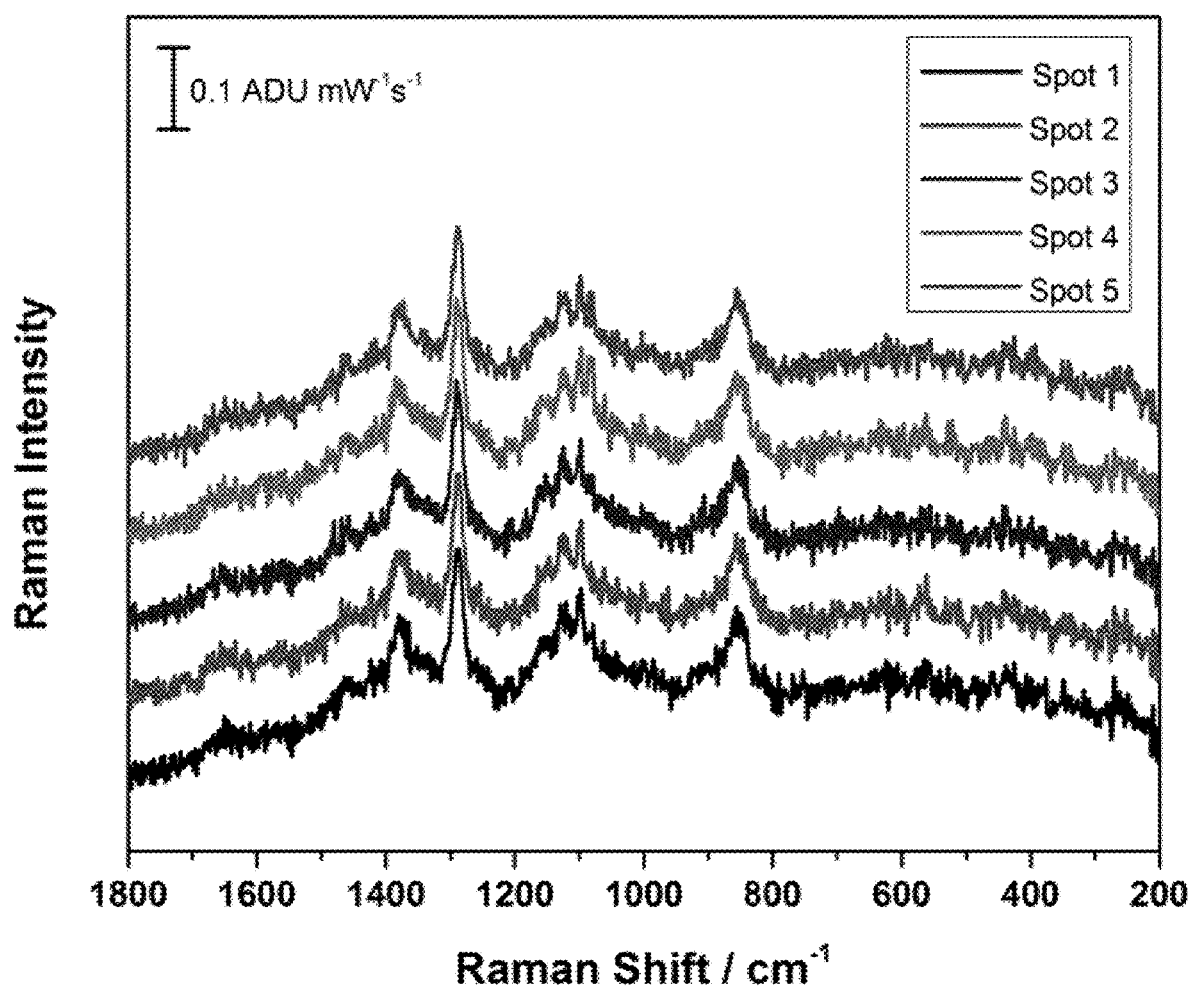
FIG. 3 shows Raman spectra of test materials (3D diagnostic substrate)

In this regard, FIG. 3 provides the Raman spectra of an example of a diagnostic substrate, in this case a 3D nitrocellulose membrane-based diagnostic substrate. As can be seen, this membrane example has a normal Raman signal which is consistent with nitrocellulose. The Raman reporter may be selected so as to avoid the peaks occurring in the diagnostic substrate Raman spectra. As shown, the Raman spectra of the diagnostic substrate example provided in FIG.

3 is highly consistent, indicating that it may be useful as an internal standard or control in certain applications.

Example 3

Diagnostic Substrate and Nanoparticle Characterization

Figure 4:
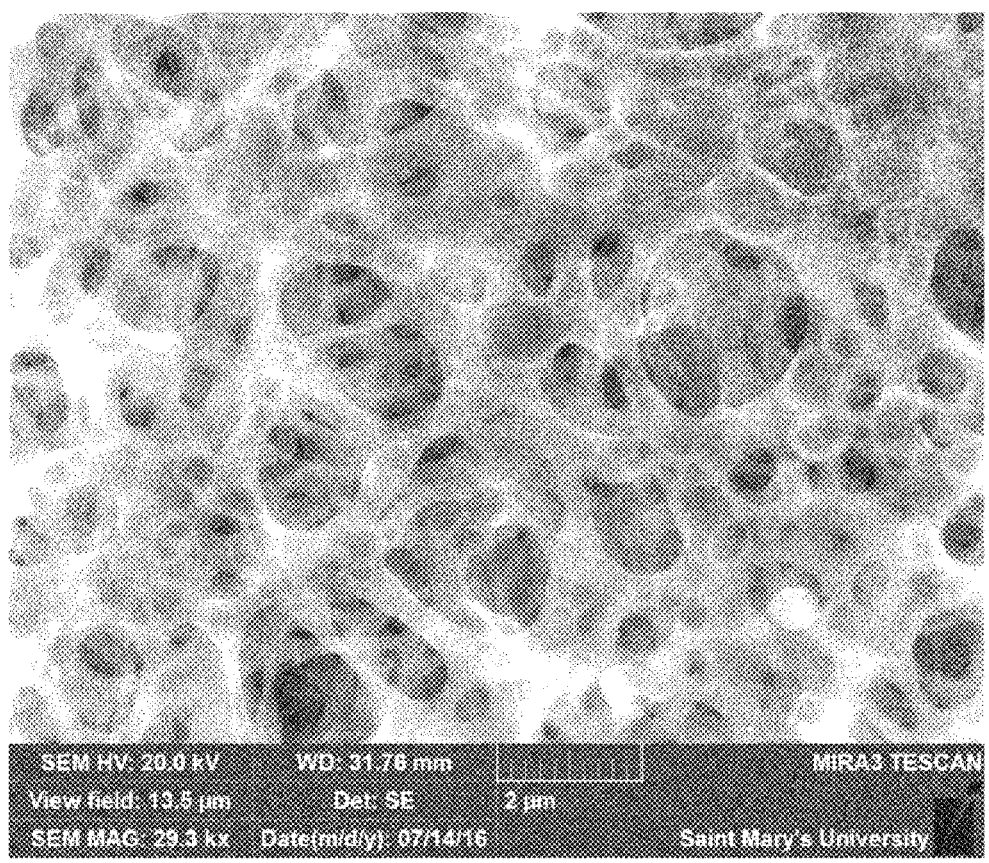
FIG. 4 shows a microscopy image of nitrocellulose membrane-based 3D diagnostic substrate, showing pore diameter.

The diagnostic substrate may also be chosen so as to provide a suitable porosity and/or Wicking power to allow for suitable binding of capture agent, flow rate, and/or assay sensitivity for a particular application. In this regard, FIG. 4 shows a microscopy image of a nitrocellulose membrane-based 3D diagnostic substrate, showing that pore diameter in this diagnostic substrate example varies from a few hundred nm to several microns.

Figure 5:
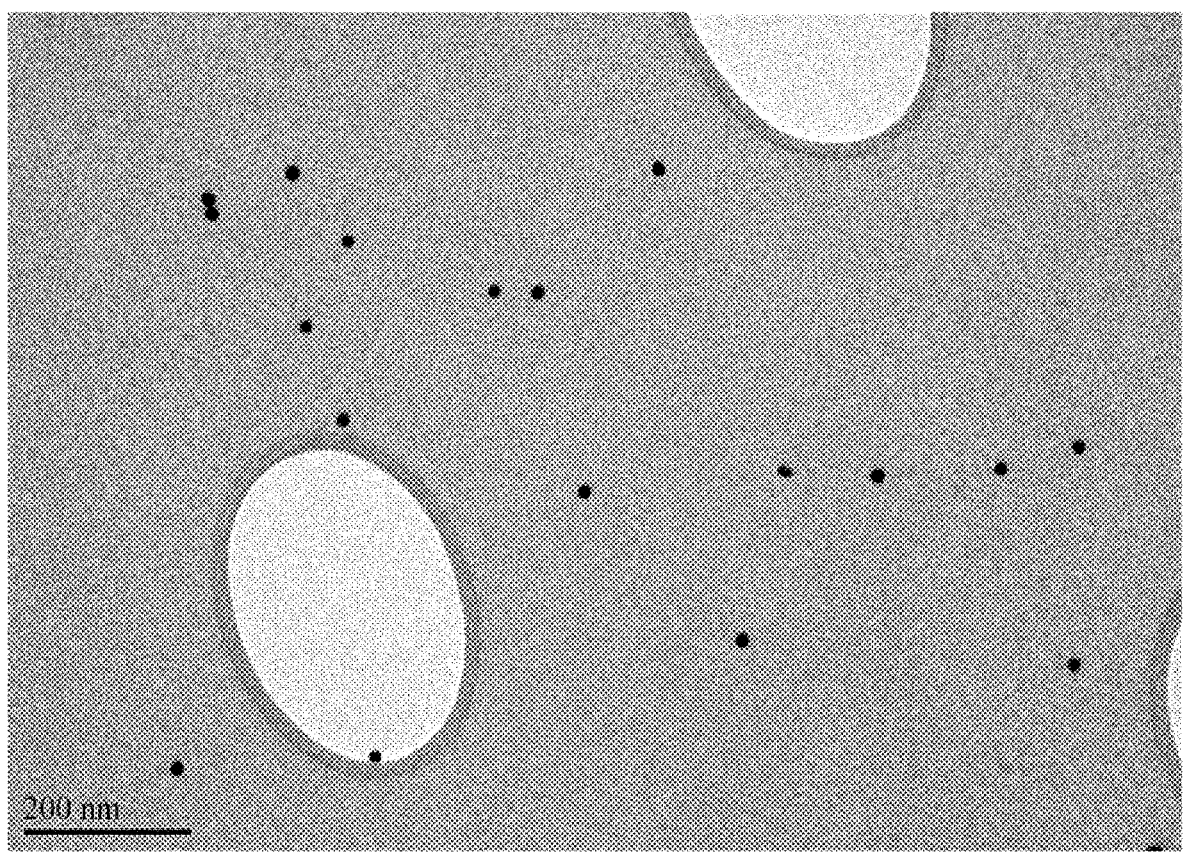
FIG. 5 shows a microscopy image showing average nanoparticle diameter.

In embodiments, where a SERS effect is desirable for increasing sensitivity, a Raman detection agent may be used which comprises a Raman signal-enhancing metal nanoparticle or colloidal particle which contributes a Raman enhancement effect. The Raman signal-enhancing metal nanoparticle may thus comprise a gold nanoparticle (AuNP), for example. FIG. 5 shows microscopy images showing average nanoparticle diameter of an in-house AuNP prep. The exemplified AuNPs (n=18) had a mean diameter of 13.0 nm, with an SD of ±2.7 nm, a Min of 9.0 nm, and a Max of 18.2 nm. The AuNP prep was substantially monodisperse. Larger AuNPs may allow for stronger SERS enhancement.

Indeed, SERS enhancement is believed to be a function of nanoparticle size. Without wishing to be limited by theory, it is believed that as particle size increases, there may be an increase in surface coverage of the Raman reporter, and the plasmon band may increase, an indication of enhanced electromagnetic enhancement. Further discussion may be found in Joseph, V., et al., *J, Raman Spectrosc.*, 2011, 42:1736-1742 (herein incorporated by reference in its entirety). Thus, in certain embodiments, AuNPs of about 40 nm in diameter or larger may be used where strong SERS effect is desirable.

Example 4

Exposure of Analyte-bound Diagnostic Substrate to Nanoparticles

As will be understood, methods described herein may include a step of exposing the diagnostic substrate to nanoparticles which bind to the diagnostic substrate via binding to the analyte, or to a complex formed between the analyte and the capture agent. In such embodiments, the nanoparticles sufficiently bind so as to allow for subsequent detection of the Raman detection agent on the diagnostic substrate using Raman spectroscopy.

Figure 6:
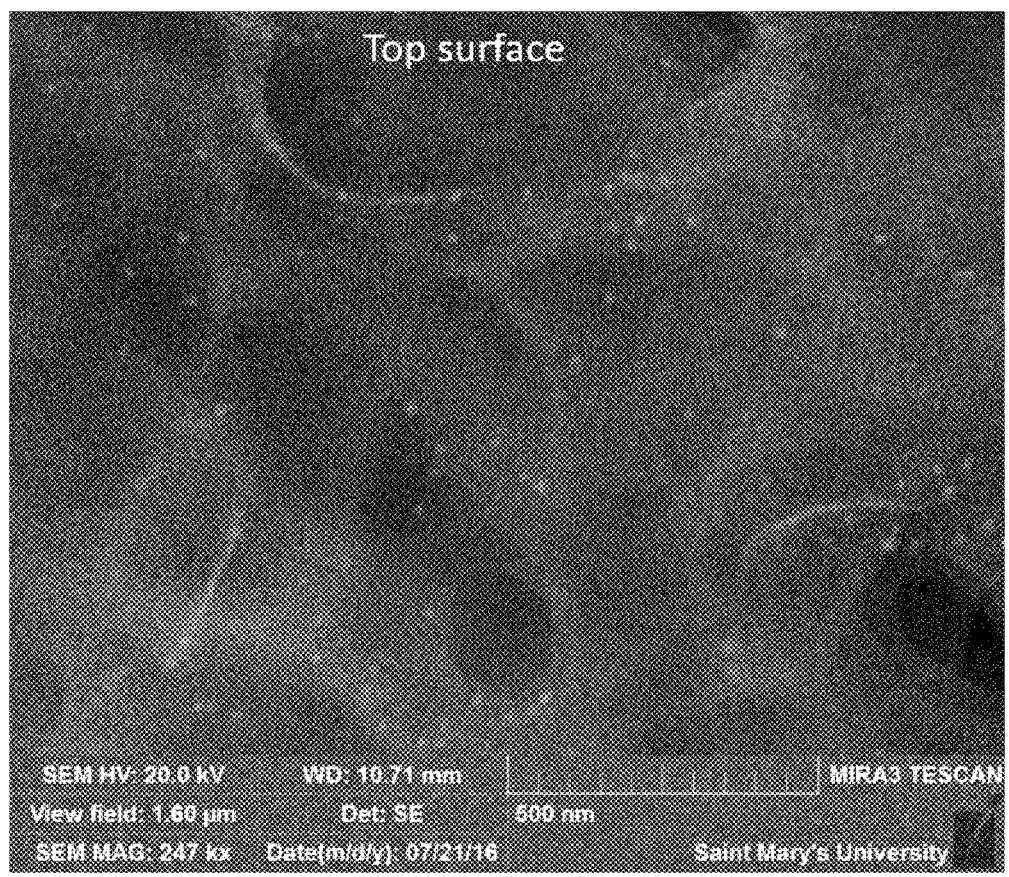
FIG. 6 shows a top surface microscopy image of a 3D diagnostic substrate which has been exposed to nanoparticles.
Figure 7:
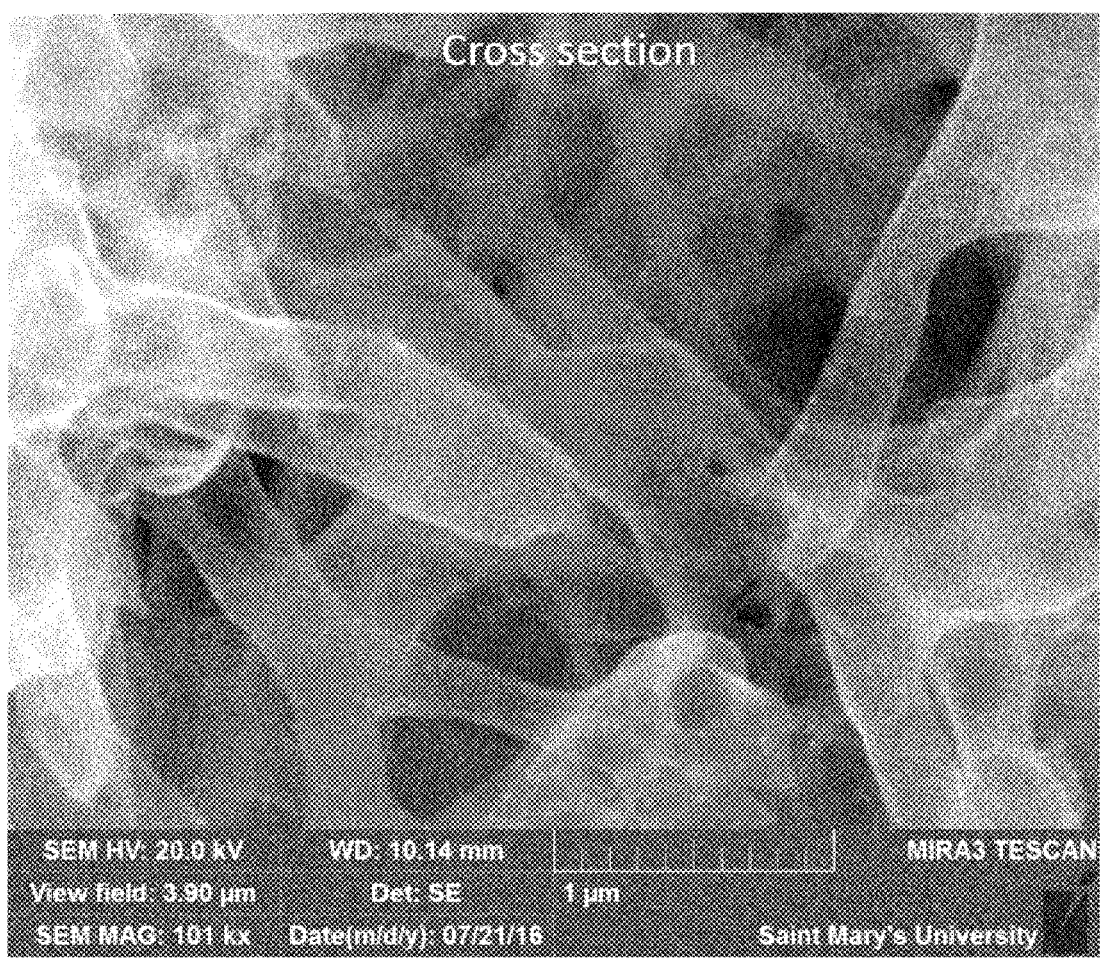
FIG. 7 shows a cross section microscopy image of the 3D diagnostic substrate which has been exposed to nanoparticles, as shown in FIG. 6.

FIGS. 6 and 7 show top surface (FIG. 6) and cross section (FIG. 7) microscopy images of an example 3D diagnostic substrate. In this example, a capture agent, antigens derived from conserved regions of the HCV antigens, were applied to the nitrocellulose membrane. After the nitrocellulose membrane was allowed to dry at room temperature in an area where the relative humidity was less than 40%, the membrane was exposed and used to perform an assay. Briefly, a liquid sample containing the analyte, anti-HCV antibodies, was applied to the diagnostic substrate and allowed to absorb into it. As it absorbed, the analyte bound to the capture agent, forming a complex. Nanoparticles were subsequently added to the diagnostic substrate where they bound to the capture agent-analyte complex. Presence is observable as circular dots.

Figure 8:
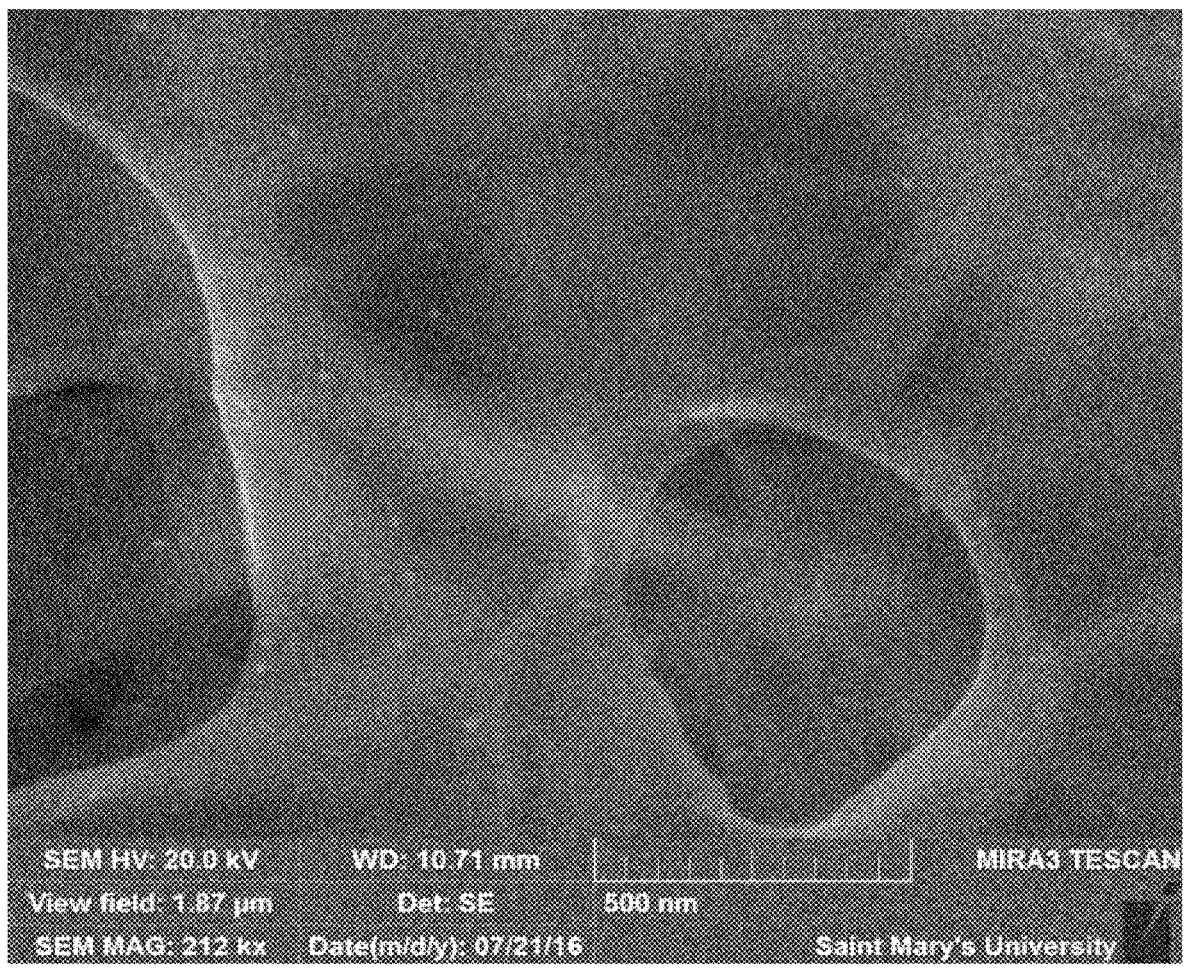
FIG. 8 shows a microscopy image of a 3D diagnostic substrate which has been exposed to nanoparticles.

Nanoparticles are easily identifiable in the top surface and cross section views of FIGS. 6 and 7. FIG. 8 provides another top surface view of a second field of view on the same diagnostic substrate. Collectively, as can be seen in the SEM images, analyte binding to capture agent, and detection of binding, occurs well below the upper surface of the diagnostic substrate. Of note in this example, SEM was used to observe the presence of nanoparticles. It will be understood, however, that presence of Raman detection agent, via the Raman reporter, may be more typically done via Raman spectroscopic analysis.

Example 5

Raman Detection Agent Selection

As will be understood, Raman detection agents as described herein comprise an affinity component, which may be joined to a Raman signal-enhancing nanoparticle. The affinity component may be selected so as to provide binding to the analyte, or to a complex formed between the analyte and a capture agent, on the diagnostic substrate when the Raman detection agent is exposed thereto. The affinity component may be selected so as to provide a suitable linkage between the analyte/diagnostic substrate and the Raman detection agent so as to allow the Raman detection agent to remain associated with the diagnostic substrate during subsequent Raman analysis step(s).

Furthermore, Raman detection agents as described herein comprise a Raman reporter, which may be joined to the Raman signal-enhancing nanoparticle. The Raman reporter may be selected so as to provide a signal detectable by Raman spectroscopic analysis once the Raman detection agent has bound to the analyte, or a complex formed between the analyte and a capture agent, on the diagnostic substrate. The Raman reporter may be selected so as to provide a suitable signal detectable by Raman spectroscopy, and so as to suitably bind to the Raman signal-enhancing nanoparticle such that the Raman reporter remains associated thereto during subsequent Raman analysis step(s).

Figure 9:
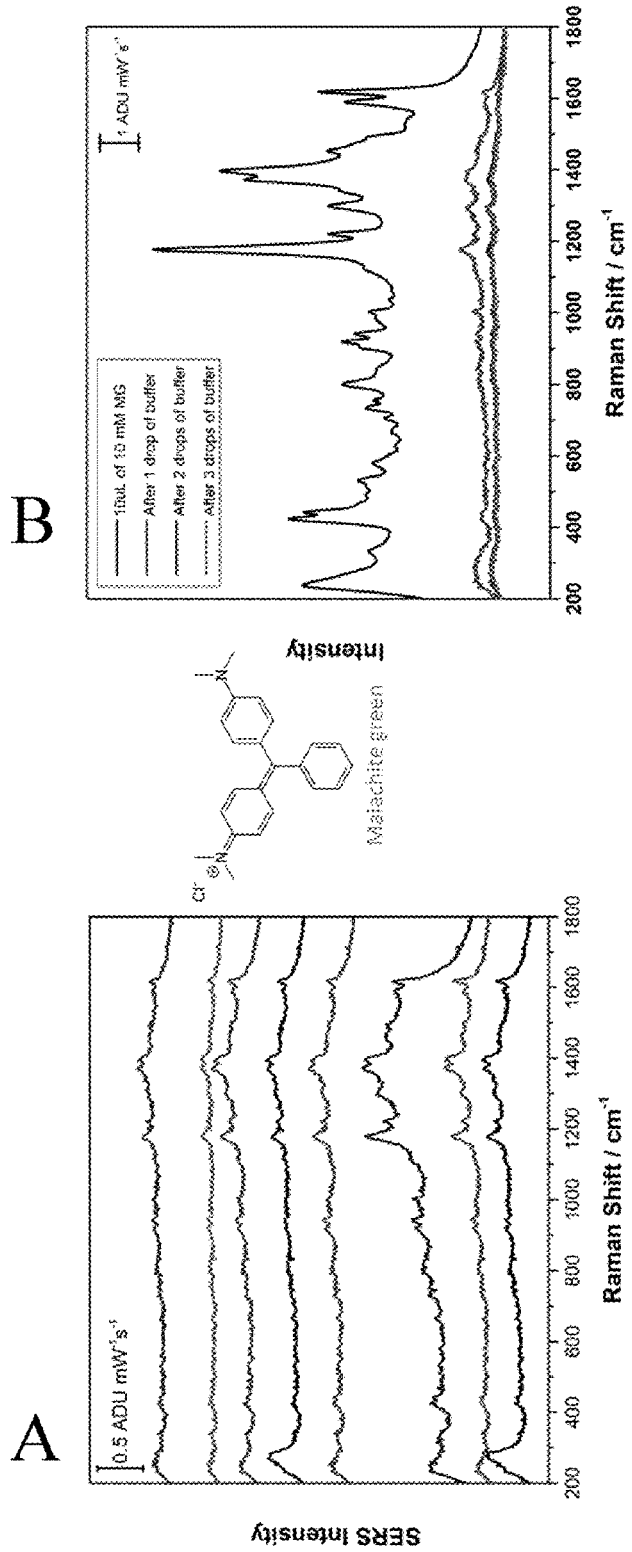
FIG. 9 shows Raman spectra of malachite green Raman reporter mixed with AuNPs, and dropped onto a 3D diagnostic substrate membrane (A), and changes in signal intensity following buffer addition (B)

FIG. 9 shows an evaluation of a Raman detection agent comprising an AuNP carrying a malachite green Raman reporter. In this example, 10 µM malachite green was mixed with AuNPs, and then drop cast onto a diagnostic substrate membrane. Although SERS signals could be observed (A), the signal was non-uniform. Further, the addition of buffer caused the signal to disappear (B). These results suggested that malachite green was not an optimal Raman reporter for this particular application, as its association with the AuNPs used may not have been suitable to withstand the experimental conditions being used.

Figure 10:
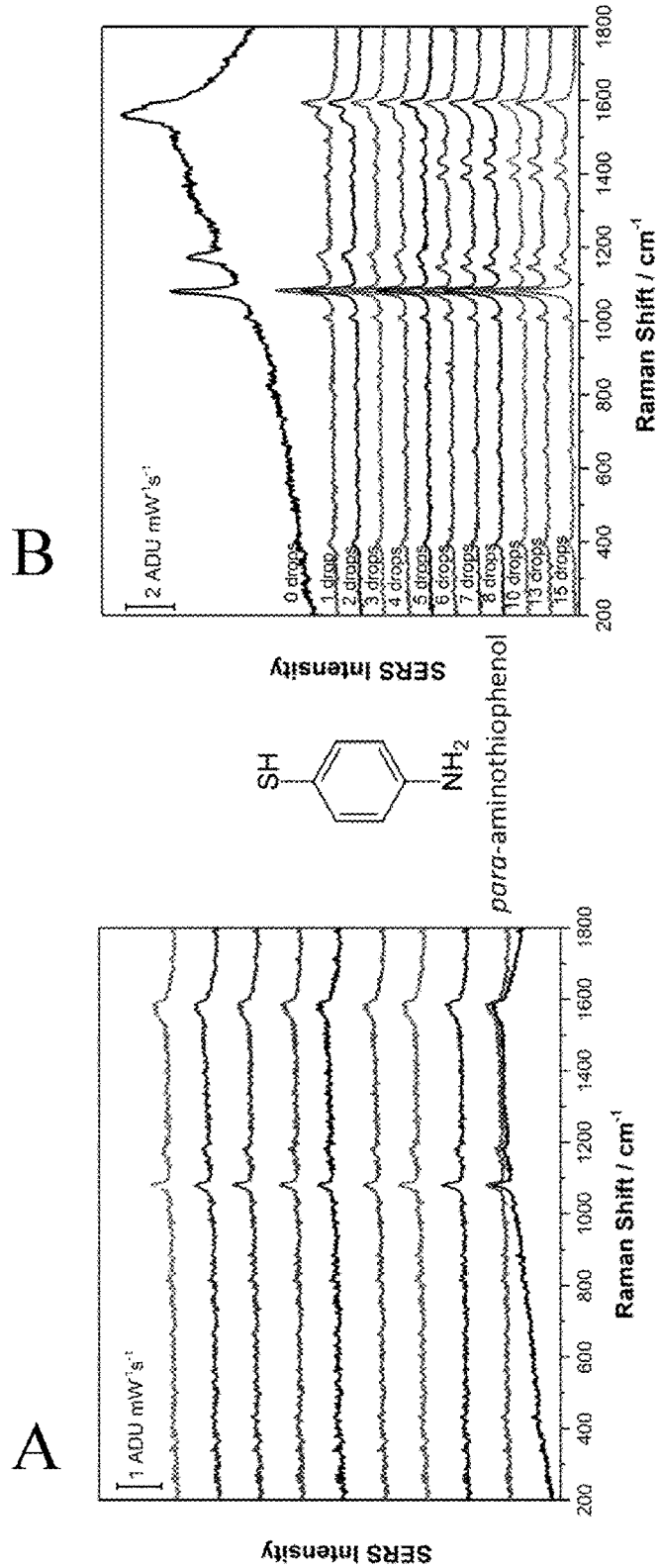
FIG. 10 shows Raman spectra of para-aminothiophenol Raman reporter mixed with AuNPs, and dropped onto a 3D diagnostic substrate membrane (A), and signal intensity following buffer addition (B)

FIG. 10 shows an evaluation of a Raman detection agent comprising an AuNP carrying a para-aminothiophenol (pATP) Raman reporter. In this example, results suggest that pATP had stronger binding affinity for the AuNPs used (possibly through formation of Au—S bonds), thus providing a strong SERS signal (A), which improved with addition of buffer (B). These results indicate that pATP was a good Raman reporter candidate for the experimental conditions being used.

Example 6

Raman Detection Agent Preparation

As will be understood, Raman detection agents as described herein may comprise both an affinity component and a Raman reporter, both of which may be joined to a Raman signal-enhancing nanoparticle.

Figure 11:
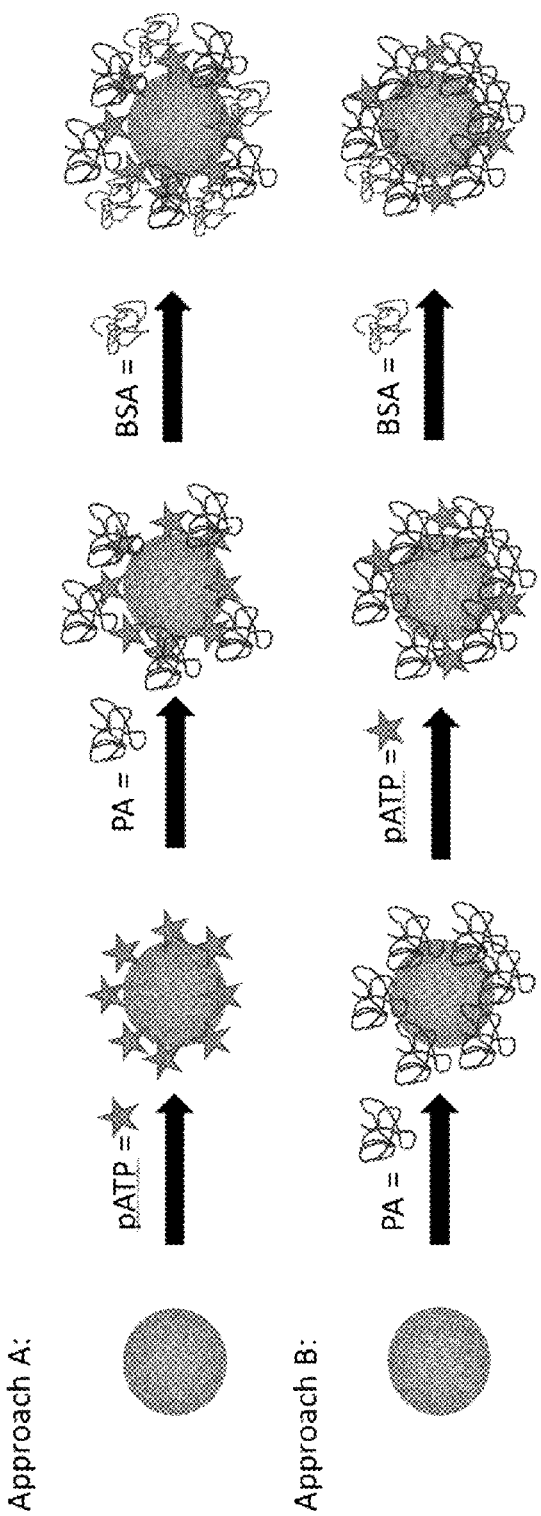
FIG. 11 shows Approach A and Approach B for generating embodiments of Raman detection agents.

FIG. 11 shows two potential approaches (Approach A and Approach B) contemplated for generating embodiments of Raman detection agents. In Approach A, Raman signal-enhancing nanoparticle is first derivatized with the Raman reporter (in this example, pATP), and then joined with the affinity component (in this example, protein A), and then, optionally, exposed to a blocker (in this example, BSA). In Approach B, Raman signal-enhancing nanoparticle is first derivatized with the affinity component (in this example, protein A), and then joined with the Raman reporter (in this example, pATP), and then, optionally, exposed to a blocker (in this example, BSA).

Example Raman detection agents were prepared using each of Approaches A and B. Samples 1-3 in FIG. 12 were prepared using Approach A, and samples 4-6 were prepared using Approach B. AuNPs were used, along with protein A, pATP, and BSA, in the quantities shown in FIG. 12. As can be seen, using these reagents and experimental conditions, analyte detection tests using these Raman detection agents were successful in 5 of 6 cases (sample 1 exhibited too much aggregation). Furthermore, sample 4 prepared according to Approach B demonstrated notable SERS enhancement.

Figure 13:
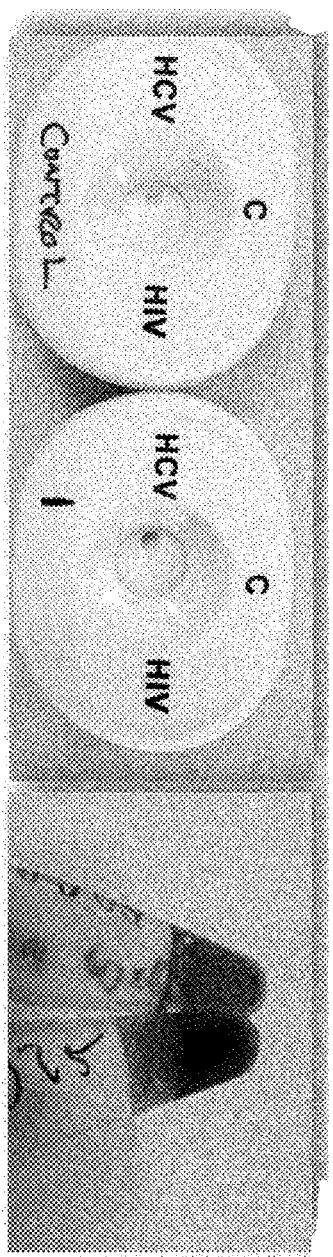
FIG. 13 shows parameters and analyte detection results obtained for a particularly effective Raman detection agent.

Based on the results provided in FIG. 12, several additional studies were performed in order to further optimize the Raman detection agents. Studies altered amount of pATP (thiol), increased time for the thiol step, removed BSA blocking step, and tested other such parameters. FIG. 13 shows a particularly useful combination which provided good results in this testing. In this combination, AuNPs (990/μL) were exposed to 10 μL of 1 mg/mL protein A, 1 μL of 1% BSA, and 390 μL of 0.1 mM pATP, according to Approach B. It will be understood that this combination is but one example, and is not intended to be limiting in any way. Other combinations, conditions, and/or optimizations may be possible, as will be understood by the person of skill in the art having regard to the teachings herein.

Analyte was successfully detected on the diagnostic substrate, and strong SERS signal was observed.

Example 7

Raman Spectroscopic Analysis; Intensity and Reproducibility

Figure 14:
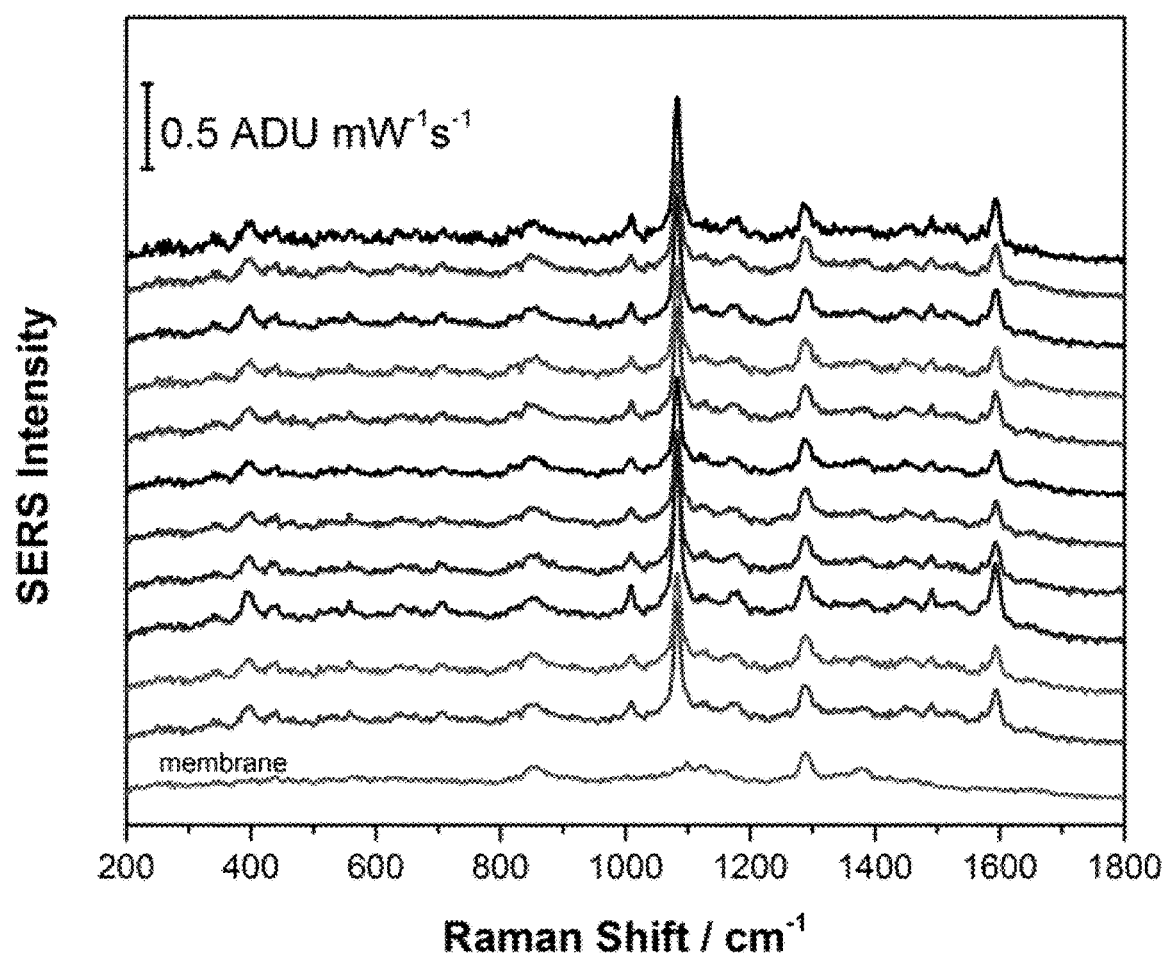
FIG. 14 shows Raman spectra collected for 10 different regions within a developed test spot, demonstrating that variation was minimal.

Using a Raman detection agent and diagnostic substrate as described hereinabove in Example 6 and Example 4, Raman spectroscopy was used to analyse SERS signal. Raman spectra were collected for 10 different regions on a developed reaction zone of the diagnostic substrate to assess variability across a single spot (about 100 μm in size) on the diagnostic substrate. As shown in FIG. 14, the variation was minimal, with spectra having on average 98% correlation with one another. These results demonstrate minimal variation, indicating that such systems may provide for quantitative detection. Reproducibility in this example is even comparable to certain liquid-based Raman analytical approaches.

In traditional approaches, wherein analysis is completed on 2D diagnostic substrates, Raman spectra obtained following completion of an assay may vary when moving between regions of the diagnostic substrate. Significant variability may be observed in various parts of the diagnostic substrate. In certain examples, variability of up to 50% might be seen in some examples. Some areas of such diagnostic substrates may be devoid of Raman label, while others may have significant quantities of label, which are known as "hot spots". As such, traditional Raman analysis often involves scanning large surface areas so as to allow for averaging to be performed in an effort to increase reproducibility.

Results obtained herein at FIG. 14 indicate that by exposing the sample to a 3D diagnostic substrate presenting a capture agent for the analyte, and exposing the diagnostic substrate to a Raman detection agent comprising a Raman signal-enhancing metal nanoparticle carrying both a Raman reporter and an affinity component for binding to the analyte (or a complex formed between the analyte and the capture agent), reliable and reproducible analyte detection may be achieved using Raman spectroscopy analysis under the conditions tested.

Example 8

Raman Spectroscopic Analysis: Intensity

Figure 15:
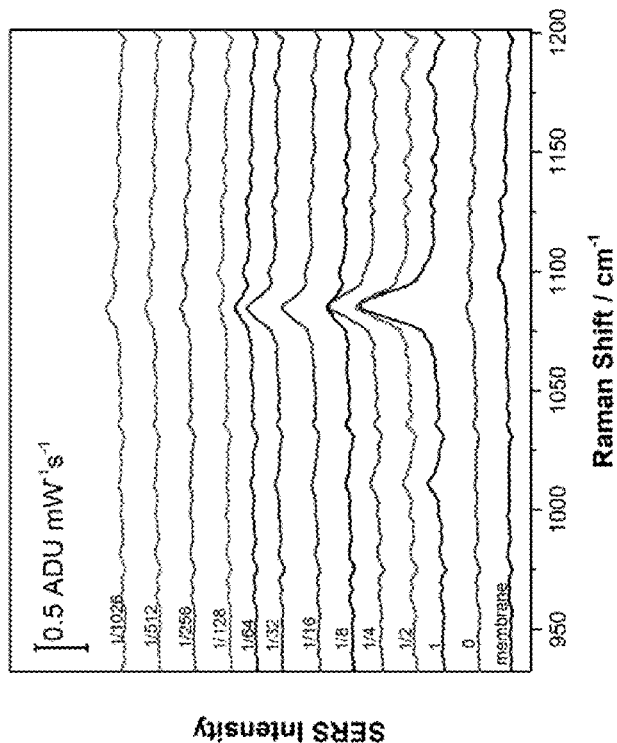
FIG. 15 shows additional Raman spectra (full spectra in (A), zoomed spectra in (B)) collected at various dilutions investigating limits of detection.
Figure 15:
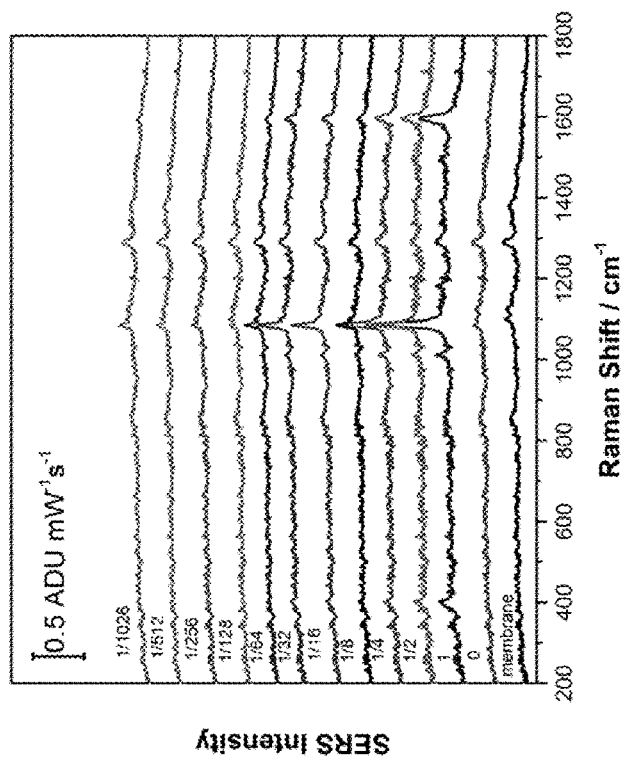

As shown in FIG. 15, dilutions were performed to illustrate dose response/limits of detection of the Raman detection agents and diagnostic substrates described in the above examples. The peak at 1080 $cm^{-1}$ was used, as it was the most intense peak associated with pATP and therefore a good candidate for limit of detection (LOD) studies (see FIG. 15). Results indicate that signal which is three times as intense as the standard deviation of noise was observed down to 1/64 dilution, after which the signal became difficult to discern over background in the conditions tested, indicating good sensitivity. As described above, it may be possible to improve sensitivity even further through adjusting of AuNP parameters such as size. Results also illustrated decreasing Raman signal generation when decreasing quantity of analyte was added.

Example 9

Batch-to-Batch Reproducibility

Example 7 presented data illustrating reproducibility observed when assessing the diagnostic substrate within a region where capture agent had been applied. In Example 7, multiple spots within the diagnostic substrate of a single test device were assessed using Raman spectroscopy to determine reproducibility observed. 98% reproducibility was observed in the conditions tested.

Figure 16:
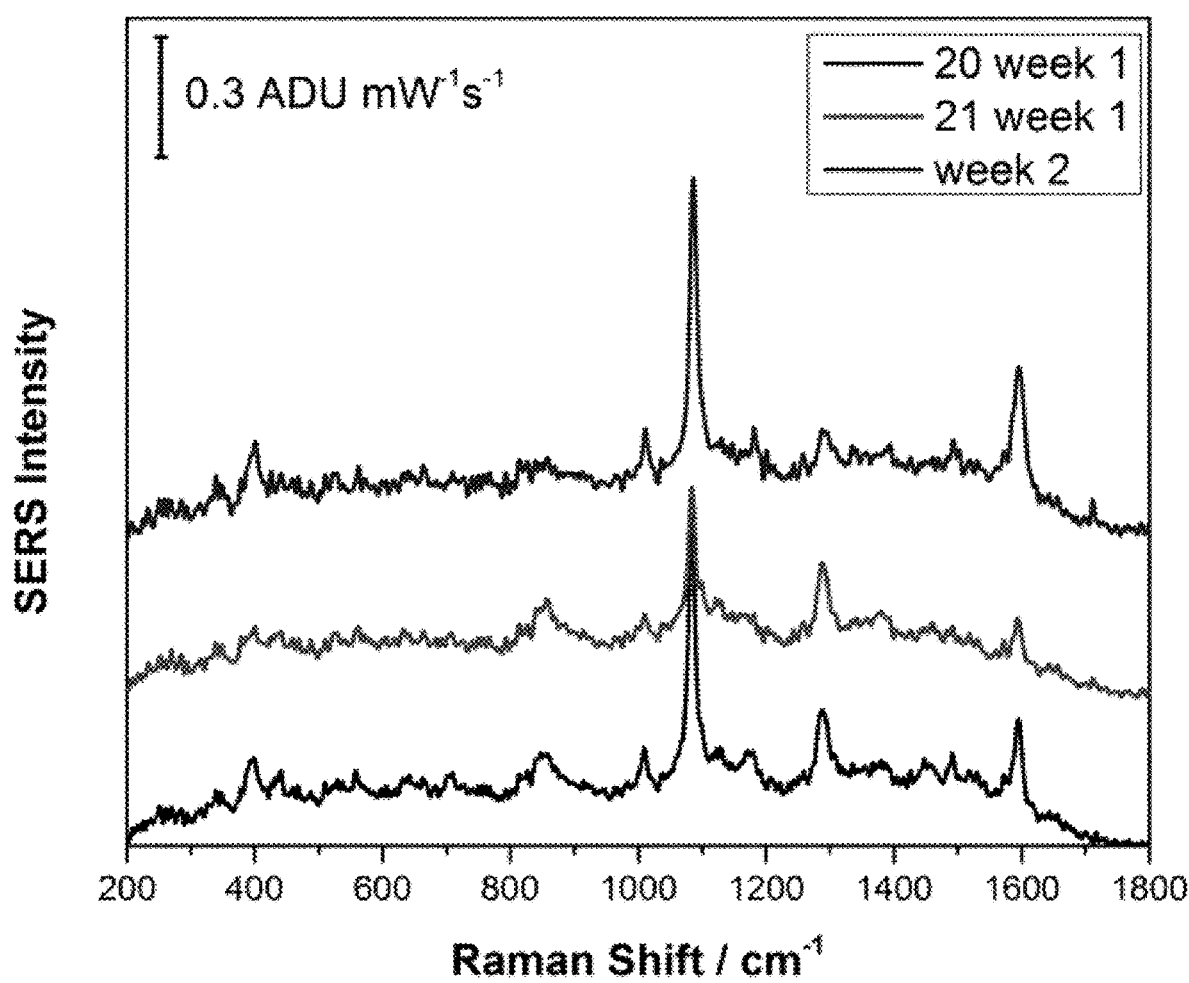
FIG. 16 shows Raman spectra showing batch-to-batch reproducibility.

To assess batch-to-batch reproducibility, two different samples (Sample 20 and Sample 21) were prepared on the same day, and one sample (Week 2) was prepared the following week from scratch. As shown in FIG. 16, batch-to-batch reproducibility between these samples was excellent, with 94-97% agreement between spectra under the conditions tested.

Example 10

Sers-Based Rapid Vertical Flow (RVF) Detection of Analyte

In this example, an example of a SERS-based rapid vertical flow (RVF) detection of analyte is described. The analyte in this example is anti-HCV antibodies. In this example, high quality and reproducible SERS spectra were obtained using AuNPs-based Raman detection agents under the conditions tested. Serial dilution studies indicated that the coupling of SERS with RVF tested in this example provided for excellent sample analysis under the conditions tested.

Vertical flow assays utilize gravity to pull the sample through a thick porous membrane or other diagnostic substrate which contains capture agent. The SERS-based RVF platform in this example utilized interaction between synthetic and recombinant antigens derived from conserved region of hepatitis C viral proteins (i.e. capture agent) that are spotted onto the test membrane (i.e. 3D diagnostic substrate), and anti-HCV antibodies that would be in an infected patient's blood sample as analyte. The resultant immune complexes were detected using a direct label Raman detection agent.

Experimental

Reagents, Solutions and Materials para-aminothiophenol (p-ATP, 97%) was used as Raman reporter for this example, and was purchased from Sigma Aldrich. Protein A from Staphylococcus aureus (salt-free, lyophilized powder) and bovine serum albumin (lyophilized powder, ≥96%) were also purchased from Sigma Aldrich. Gold chloride (ACS reagent, ≥49% Au basis, Sigma Aldrich), sodium citrate (ACS reagent, ≥99.0%, Sigma Aldrich), sodium carbonate (ACS reagent, ≥99.5%, Sigma Aldrich) and sodium bicarbonate (ACS reagent, ≥99.7%, Sigma Aldrich) were used in the preparation of the Au colloids used in this work. All solutions were prepared using Millipore water (≥18.2 MΩ cm). Miriad™ HCV/HIV Rapid Vertical Flow (RVF) assays multiplexed for hepatitis C virus (HCV) and human immunodeficiency virus ½ (HW) and were supplied by MedMira Laboratories Inc. for testing. A monoclonal antibody specific for HCV antigens was dialyzed against PBS at a concentration of 3.4 mg/mL and supplied by Cedarlane. All glassware for this research was cleaned by immersion in neat sulfuric acid overnight, followed by careful rinsing with Millipore water.

Preparation of Au Nanoparticles and Surface Functionalization

~13 nm gold nanoparticles (AuNPs) were prepared using standard methods. Briefly, 1 mL of a 1% aqueous $HAuCl_4$ solution was added to 99 mL of water and was poured into an Erlenmeyer flask. The flask was placed on a hot plate/stirrer, to bring the bare gold solution to boil while stirring, 5 mL of a 1% sodium citrate solution was added. The reaction solution was under reflux conditions for 30 minutes until a wine red color was reached. The gold nanoparticles were then allowed to cool to room temperature. Once the gold nanoparticles were prepared, 10 µL of a 1.0 mg/mL protein A solution prepared in water was added to 990 µL of the AuNP colloidal solution in an Eppendorf tube. The tube was then placed on an orbital shaker platform for 30 minutes at room temperature. Next, 390 µL of 0.08 mM p-ATP was added to the tube containing the protein A-modified AuNPs, and gently aspirated several times with the pipette tip followed by 1.0 µL of 1.0% v/v bovine serum albumin. Then, the tube was placed back on the rocking platform shaker for an additional 30 minutes. Once complete, the sample was centrifuged at 15,000 rpm for 30 minutes (Labnet PRISM microcentrifuge, Edison, N.J., USA). The supernatant was then removed, and the pellet was reconstituted with 100 µL of capping buffer. The capping buffer was composed of PBS saline, synthetic polymers, and anti-microbial agents.

Preparation of Miriad™ RVF Test Cartridge

For comparisons, Miriad RVF assays were obtained from MedMira Laboratories Inc. The assays include (1) A buffer used to complete the procedural steps which is comprised of a mixture of tris-buffered saline, lytic agents, synthetic polymers, and anti-microbial agents, (2) A test cartridge containing an absorbent pad that is in direct contact with a nitrocellulose membrane where capture agents capable of binding to anti-HCV and anti-HIV antibodies have been applied in discrete locations, and (3) A direct label comprising protein A affinity component conjugated to a colloidal gold particle impregnated in a filter medium housed in a plastic carrier (InstantGold™ cap)). The assay was used according to the package insert, for the purposes of comparison with SERS-based approached as described herein. Briefly, this involves addition of three drops of the buffer to the test cartridge, followed by addition of one drop (~30 µL) of sample (anti-HCV monoclonal antibodies were used in this example to simulate a hepatitis-C positive patient specimen). Next, the InstantGold™ cap, is placed onto the cartridge and 12 drops of buffer are added to the cap. The cap is removed once all the solution has been absorbed, and the test spot is then read after application of three drops of buffer to clear the background of the membrane. For the qualitative visual determination, this procedure was followed exactly as stated.

For SERS analysis according to methods as described herein, the InstantGold™ cap step of the comparator assay was replaced with the addition of 30 µL of the fully functionalized Raman detection agent (in this example, the AuNP-based Raman detection agents prepared as described immediately above). After this step, the 12 drops of buffer were then added to the test cartridge as stated previously for the comparator test. In both cases, at the end of the test procedure the membrane-based diagnostic substrate was washed with three more drops of buffer.

Instrumentation

Raman and SERS experiments for the developed RVF test cartridge were conducted using a DeltaNu benchtop Raman spectrometer equipped with a 785 nm laser (Intevac Photonics, Santa Clara, USA). The spectrometer resolution was 5 $cm^{-1}$ and it was equipped with an air-cooled CCD detector and a right angle optics attachment. Sample acquisition time was 30-60 seconds at laser powers ranging between 10.6-55.9 mW. All Raman data is corrected for both laser power and acquisition time. Origin 8.1 was used for the spectral processing and data analysis (OriginLab Corporation, Northampton, Mass., USA). FIG. 17 shows the test cartridge undergoing Raman analysis.

Characterization

The initial characterization involved measurement of the extinction spectrum using UV-vis spectroscopy. This was accomplished using an Ocean Optics 2000+ USB UV-vis-NIR Spectrometer. In order to further evaluate the structure and morphology of the RVF cartridges as well as the detection agents used in this example, both FE-SEM and TEM were employed. For FE-SEM imaging, a TESCAN Mira3 LMU field emission scanning electron microscope (FE-SEM), equipped with an Oxford X-Max 80 mm2 SDD EDX detector was utilized. TEM images were acquired using a Phillips Tecnai G2 electron microscope with an operating voltage which varied between 43 and 220 kV. Samples for TEM were prepared by placing a drop of the Raman detection agent solution onto holey carbon grids purchased from Cedarlane (Burlington, Ontario, Canada). ImageJ software (National Institutes of Health, Bethesda, Md., USA) was used for image analysis where appropriate.

Results

Characterization of RVF Test Cartridge

Figure 18:
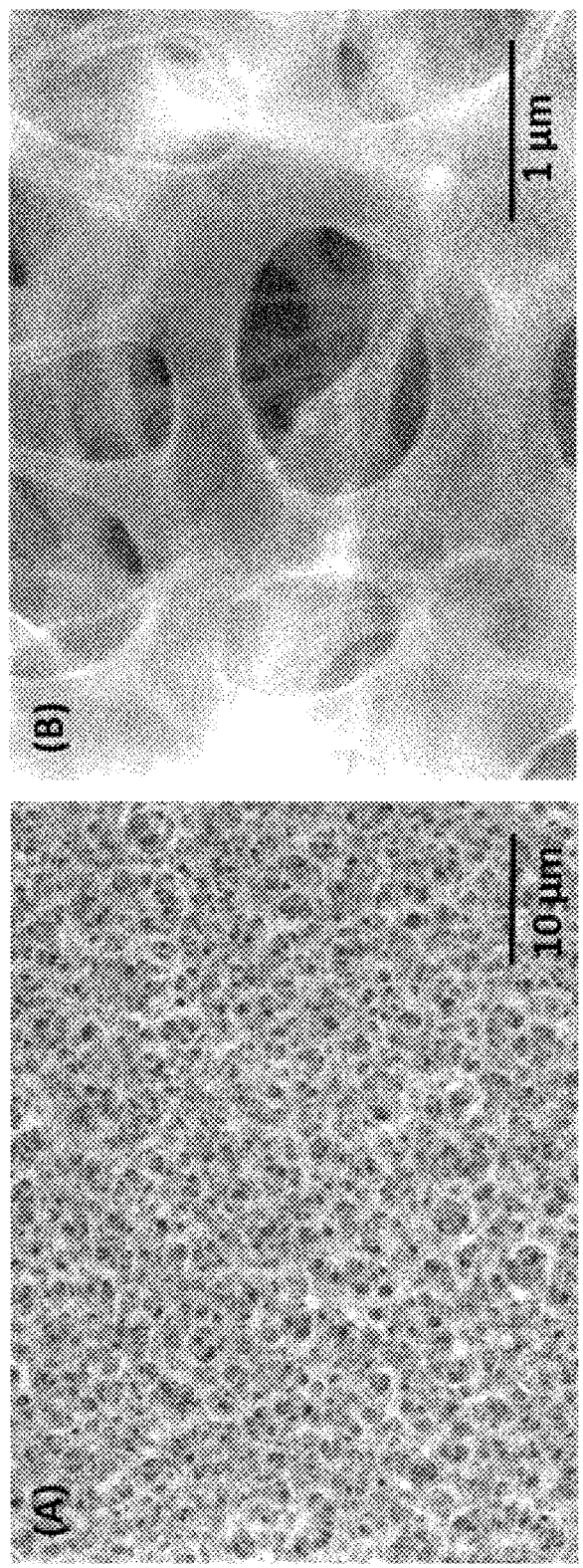
FIG. 18 shows SEM images of the surface of the RVF test cartridge membrane at low magnification (A) and high magnification (B)

FIG. 18 shows SEM images of the nitrocellulose test cartridge membrane used in this example. The porous nitrocellulose structure is evident, with pore diameters ranging from a few hundred nanometers to several microns. FIG. 3, already described hereinabove, shows the normal Raman signal for bare nitrocellulose membrane, recorded for five different spots on the same membrane surface. Several strong Raman bands were observed at 856 cm$^{-1}$, 1288 cm$^{-1}$ and 1379 cm$^{-1}$ which correspond to the v(NO), v$_s$(NO$_2$) and δ(C—H) modes of nitrocellulose, respectively. In addition, peaks between ~1050 cm$^{-1}$ and ~1150 cm$^{-1}$ due to v(C—O) for the pyranose sugars were also observed to be present.

In order to compare the limit of detection achievable by visual determination for the RVF assay with the provided InstantGold Cap versus the SERS-RVF assay of this example, a series of dilutions of the monoclonal antibody were prepared, and the test cartridge was developed according to package insert instructions using the InstantGold Cap. In this comparator, a red spot could be visualized up until 1/400 dilution, after which visual detection was no longer possible.

For the AuNP-based Raman detection agents modified with both protein A and the Raman reporter (further described below), the visual detection limit was determined to be 1/64.

Characterization of AuNPs

Initial characterization of the AuNP colloidal sol of this example was completed by measuring the extinction spectrum (sum of scattering and absorption properties) using a UV-vis-NIR spectrophotometer. The extinction maximum was observed to be at 520 nm, which is consistent with spherical AuNPs. In addition, the band was observed to be fairly narrow, an indication that the nanoparticles were fairly monodisperse. This observation was then further evaluated using transmission electron microscopy. FIG. 5, already described above, shows a representative TEM image of the bare AuNPs prepared in this study. In terms of size dispersion, with an average diameter of 12.6 nm (±1.3 nm), the gold nanoparticles were fairly monodisperse and were considered to be within an appropriate size to support localized surface plasmon resonance for SERS enhancement.

Evaluation of SERS Performance for RVF Test

Figure 19:
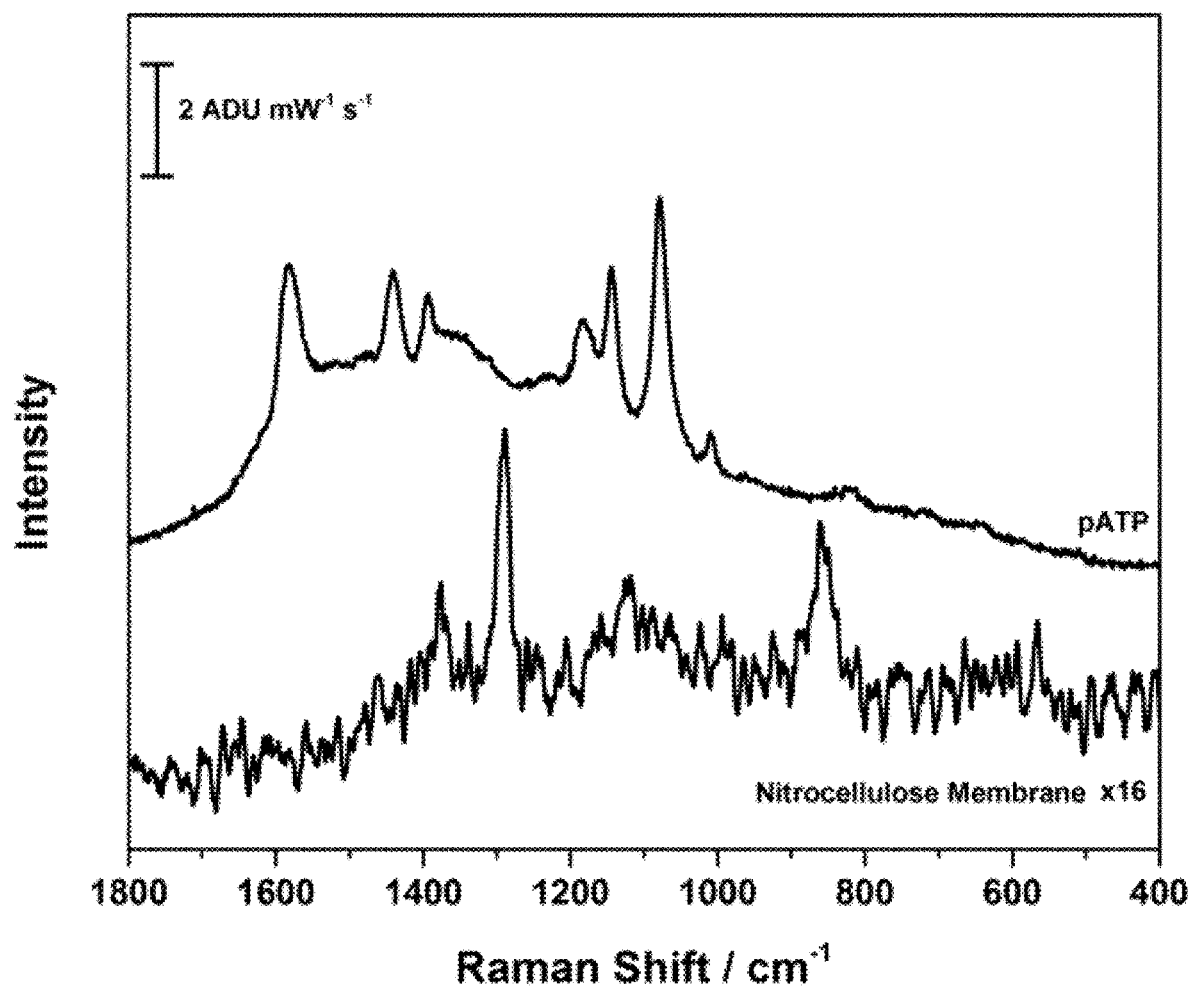
FIG. 19 shows an overlay of the normal Raman signal for nitrocellulose, with the SERS signal for p-ATP. Laser excitation was 785 nm. Power at the membrane was 22.3 mW, and acquisition time was 30 s.

As the nitrocellulose membrane had a strong Raman signature itself, a Raman reporter that would strongly bind to the AuNP surface, and also have a signal with peaks not overlapping that of the nitrocellulose, was selected. para-aminothiophenol (p-ATP) was thus chosen for this work. FIG. 19 provides an overlay of the normal Raman signal for the nitrocellulose with the SERS signal for p-ATP. As can clearly be seen, the predominant p-ATP peaks at ~1080 cm$^{-1}$ (v(C—S)) and ~1590 cm$^{-1}$ (v(C—C)), were marker peaks which do not interfere with the membrane signal.

Figure 20:
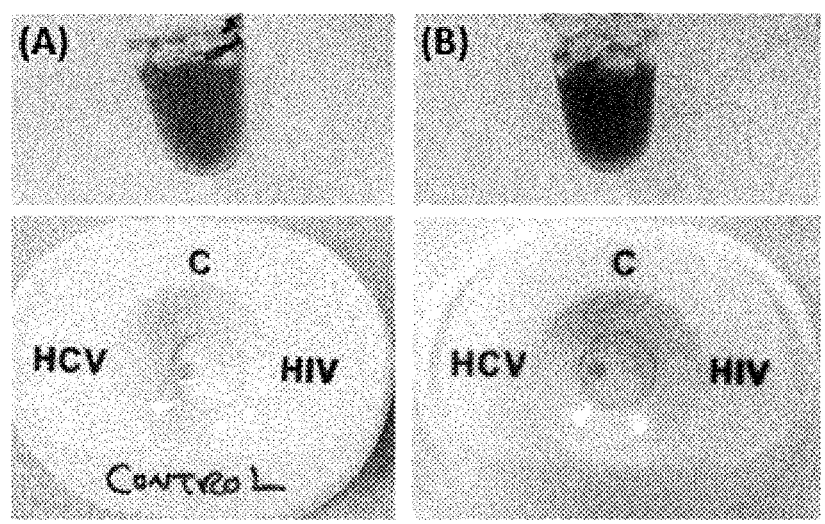
FIG. 20 shows (A) that a suspension of protein A conjugated AuNPs exhibited a red color, resulting in a red developed test spot, and (B) that the suspension of protein A and pATP conjugated AuNPs exhibited a purple color, resulting in a purple developed test spot.

SERS performance for the developed test spot was then evaluated. When the AuNPs were functionalized with p-ATP according to the procedure outlined above, a colour change was noted from red to purple after the centrifugation step, as can be seen in FIG. 20. When the modified AuNPs were then used for the test, the developed spot was also purple, as opposed to red (FIG. 20). Results indicate that, under the conditions tested, the AuNPs, once modified with the Raman reporter, maintained their functionality for immunoassay. Without wishing to be bound by theory, the red-shifted colour change may be an indication that upon modification with p-ATP, the AuNPs may be slightly aggregated. In terms of SERS enhancement, nanoparticle aggregation is well-known to be a factor which may contribute to high quality SERS signals.

Figure 21:
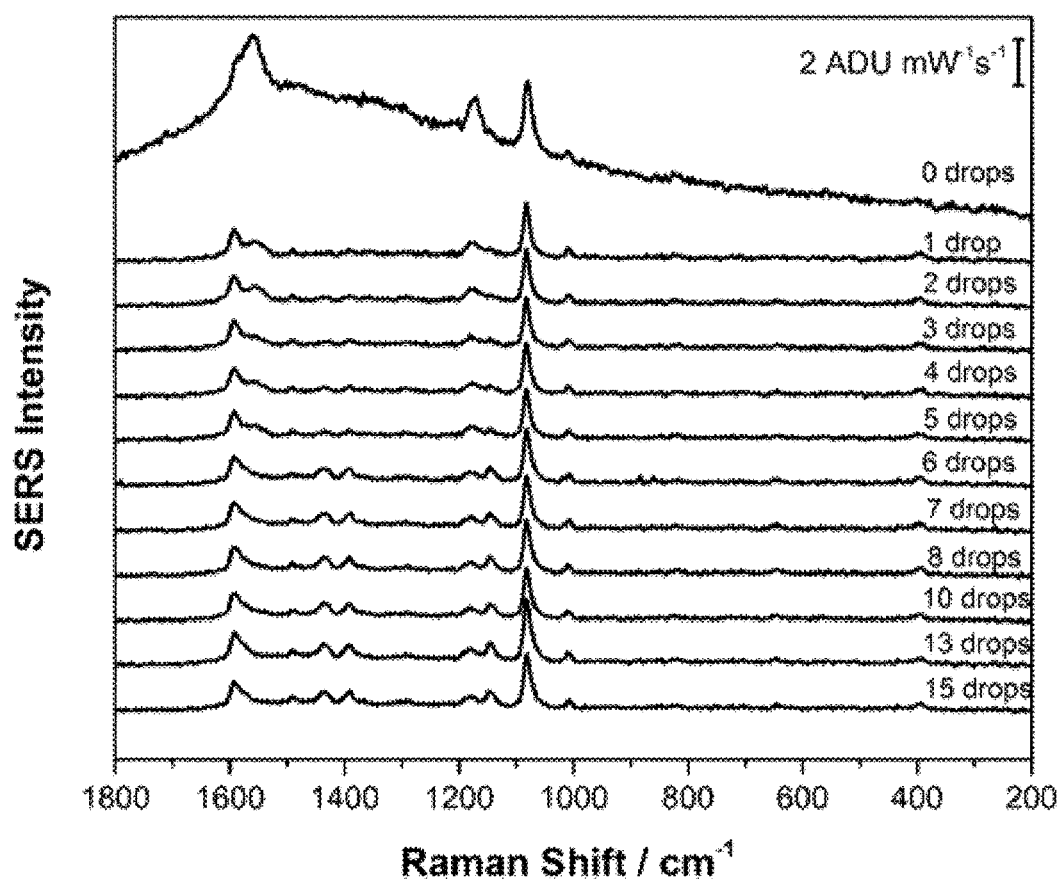
FIG. 21 shows SERS signals recorded for a developed test spot prior to the addition of buffer, and after each subsequent buffer drop. Laser excitation was 785 nm. Power at the membrane was 10.6 mW, and acquisition time was 60 s.

FIGS. 6 and 7, already described hereinabove, show SEM images of the developed test spot after the test procedure was completed with the HCV monoclonal antibody and InstantGold Cap. The AuNPs can clearly be observed on the surface of the membrane, and percolating down through the membrane. When the membrane was removed and prepared in cross-section, the AuNPs could still be observed in the deep interior of the membrane. These results suggest that the nitrocellulose membrane may function as a 3-dimensional SERS substrate, where a three dimensional focal volume is accessible for SERS signal acquisition, as opposed to a 2-dimensional focal area, as is observed for traditional non-porous SERS substrates. This observation is further supported by FIG. 21, where the SERS signal was recorded for the developed test spot prior to the addition of buffer, and after each subsequent buffer drop. With each successive drop of buffer, no (or very little) signal loss was observed, suggesting that the signal is not attenuated by dilution, and the SERS signal is coming from a focal volume.

Figure 22:
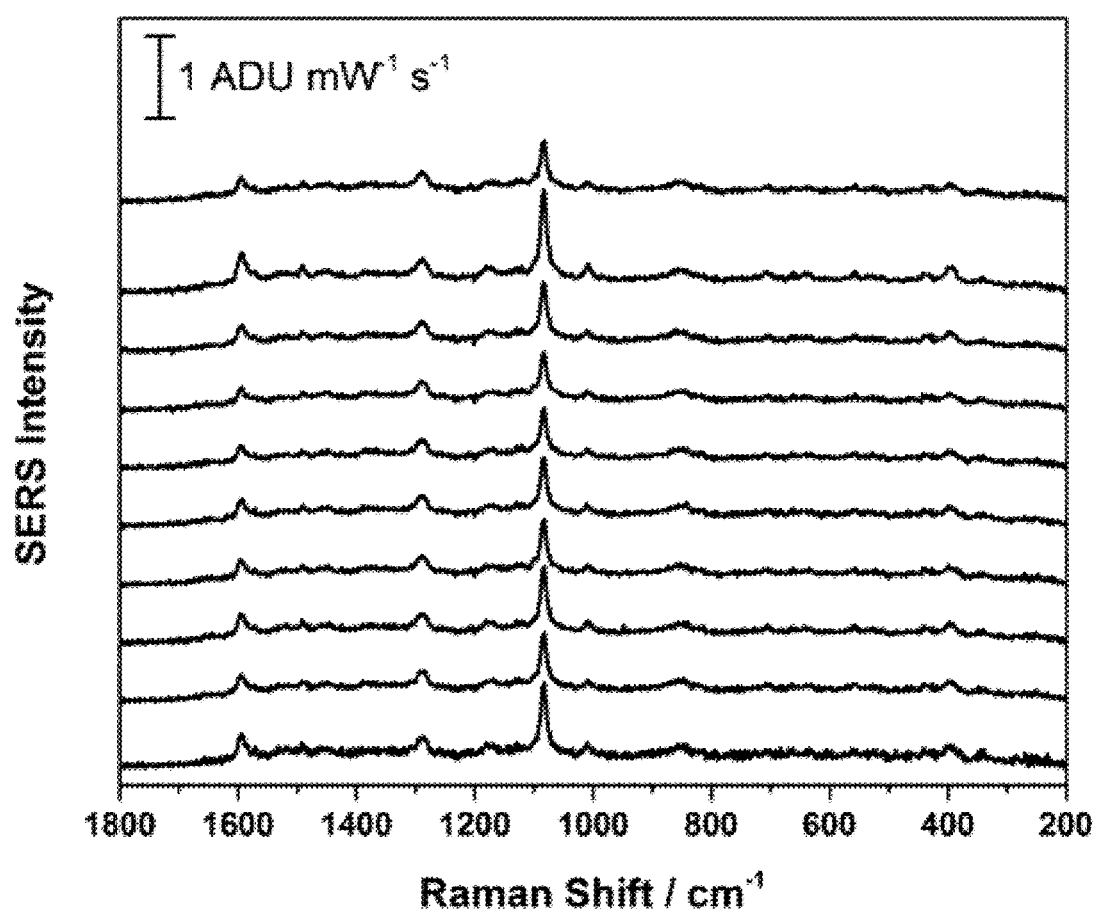
FIG. 22 shows SERS spectra collected for 10 different spots on the developed test spot. Laser excitation was 785 nm. Power at the membrane was 55.9 mW, and acquisition time was 60 s.

FIG. 22 (see, also, FIG. 14) shows the SERS spectra collected for 10 different spots on the developed test spot. This measurement simply required movement of the test cartridge by approximately a mm in order to access a new area, followed by signal collection. Since the laser spot diameter was only ~100 μm, many different areas within the developed test spot could be probed. The SERS signal observed for the Raman reporter under the conditions tested was excellent, and no significant interference from the nitrocellulose membrane was observed for the main Raman reporter peaks at ~1080 and ~1590 cm$^{-1}$. Signal for the nitrocellulose membrane was continually present, especially for the peaks at 856 cm$^{-1}$ and 1288 cm$^{-1}$. Under the conditions tested, the membrane peaks were remarkably reproducible, suggesting they may be useful for internal standardization of the SERS signal.

One or more illustrative embodiments have been described by way of example. It will be understood to persons skilled in the art that a number of variations and modifications can be made without departing from the scope of the invention as defined in the claims.

What is claimed is:

1. A method for detecting the presence of an analyte in a sample from a subject or source, said method comprising:
    providing a diagnostic substrate presenting a capture agent;
    exposing the sample to the diagnostic substrate, allowing analyte in the sample,
    if present, to bind the diagnostic substrate via the capture agent presented thereon which is specific for the analyte;
    exposing the diagnostic substrate to a Raman detection agent which binds to the diagnostic substrate via binding to the analyte, or to a complex formed between the analyte and the capture agent, if the analyte is present; and
    detecting whether the Raman detection agent bound to the diagnostic substrate using Raman spectroscopy, whereby detection of Raman detection agent bound to the diagnostic substrate indicates the presence of the analyte in the sample;
    wherein the Raman detection agent comprises a Raman signal-enhancing metal nanoparticle carrying both a Raman reporter for producing a signal detectable by Raman spectroscopy, and an affinity component for binding the analyte or the complex formed between the analyte and the capture agent on the diagnostic substrate;

wherein the affinity component comprises protein A.

2. A method for detecting the presence of an analyte in a sample from a subject or source, said method comprising:
provided a diagnostic substrate presenting a capture agent;
exposing the sample to a Raman detection agent, allowing analyte in the sample, if present, to bind the Raman detection agent via an affinity component presented thereon which is specific for the analyte, thereby forming an analyte-Raman detection agent complex;
exposing the analyte-Raman detection agent complex to the diagnostic substrate, allowing the analyte-Raman detection agent complex to bind the diagnostic substrate via the capture agent presented thereon which is specific for the analyte or the analyte-Raman detection agent complex; and
detecting whether the Raman detection agent bound to the diagnostic substrate using Raman spectroscopy, whereby detection of Raman detection agent bound to the diagnostic substrate indicates the presence of the analyte in the sample;
wherein the Raman detection agent comprises a Raman signal-enhancing metal nanoparticle carrying both a Raman reporter for producing a signal detectable by Raman spectroscopy, and the affinity component for binding the analyte;
wherein the affinity component comprises protein A.

3. A method for detecting the presence of an analyte in a sample from a subject or source, said method comprising:
providing a diagnostic substrate presenting a capture agent;
providing a Raman detection agent presenting an affinity component;
exposing the sample simultaneously to the diagnostic substrate and the Raman detection agent, allowing the capture agent, the affinity component, and analyte in the sample, if present, to form a complex which is dependent on presence of the analyte for formation; and
detecting whether the Raman detection agent bound to the diagnostic substrate using Raman spectroscopy, whereby detection of Raman detection agent bound to the diagnostic substrate indicates the presence of the analyte in the sample;
wherein the capture agent of the diagnostic substrate is specific for the analyte or a complex formed between the analyte and the Raman detection agent; and
wherein the Raman detection agent comprises a Raman signal-enhancing metal nanoparticle carrying both a Raman reporter for producing a signal detectable by Raman spectroscopy, and the affinity component for binding the analyte or a complex formed between the analyte and the capture agent on the diagnostic substrate;
wherein the affinity component comprises protein A.

4. The method according to claim 1, wherein the diagnostic substrate is a 3D diagnostic substrate having X, Y, and Z dimensions through which the capture agent is presented, and through which the sample may permeate when exposed thereto.

5. The method according to claim 1, wherein the signal detectable by Raman spectroscopy is used to quantitate the amount of analyte in the sample.

6. The method according to claim 1, wherein the Raman signal-enhancing metal nanoparticle comprises a gold nanoparticle, or a silver nanoparticle.

7. The method according to claim 1, wherein the Raman detection agent comprises substantially monodisperse nanoparticles.

8. The method according to claim 7, wherein the nanoparticles have an average diameter of about 13.0 nm ±2.7 nm, or larger.

9. The method according to claim 1, wherein the Raman reporter comprises malachite green, 4,4'-bipyridine, para-aminothiophenol (pATP), or Rhodamine 6G.

10. The method according to claim 9, wherein the Raman signal-enhancing metal nanoparticle comprises a gold nanoparticle, and the Raman reporter is pATP, wherein said pATP is bound to the gold nanoparticle through an Au—S covalent bond.

11. The method according to claim 1, wherein the diagnostic substrate comprises a nitrocellulose membrane presenting the capture agent.

12. The method according to claim 1, wherein the analyte is an antibody.

13. The method according to claim 1, wherein the capture agent comprises an antigen linked to a virus, bacteria, cancer, or other disease-related condition in a subject.

14. The method according to claim 1, wherein the Raman detection agent further comprises a blocker for preventing non-specific binding.

15. The method according to claim 1, wherein the diagnostic substrate and the Raman detection agent are configured, through capture agent, affinity component, and Raman reporter selection, for detecting the presence of and/or quantifying levels of more than one analyte in the sample from the subject or source.

16. A Raman detection agent for detecting Raman detection agent for detecting the presence of an analyte in a sample, the Raman detection agent comprising:
a Raman signal-enhancing metal nanoparticle, the nanoparticle carrying both a Raman reporter for producing a signal detectable by Raman spectroscopy, and an affinity component for binding the analyte or a complex formed between the analyte and a capture agent on a diagnostic substrate;
wherein the Raman signal-enhancing metal nanoparticle is a gold nanoparticle, the Raman reporter is pATP, the affinity component is protein A, the analyte is an antibody, and the capture agent is an antigen.

17. A method for preparing a Raman detection agent as defined in claim 16, the method comprising:
in a first step, attaching the Raman reporter to the Raman signal-enhancing metal nanoparticle; and
in a second step, attaching the affinity component to the Raman signal-enhancing metal nanoparticle.

18. The method of claim 17, wherein the method further comprises a third step of blocking the Raman detection agent to prevent non-specific binding by exposing the Raman detection agent to a blocker.

* * * * *